(12) United States Patent
Hashimoto et al.

(10) Patent No.: US 10,709,727 B2
(45) Date of Patent: Jul. 14, 2020

(54) ANTIVIRAL DRUGS

(71) Applicant: IDAC THERANOSTICS, INC., Tokyo (JP)

(72) Inventors: Shin-ichi Hashimoto, Kanazawa (JP); Shuichi Kaneko, Kanazawa (JP); Masao Honda, Kanazawa (JP); Takayoshi Shirasaki, Kanazawa (JP); Taro Yamashita, Kanazawa (JP)

(73) Assignee: IDAC THERANOSTICS, INC., Tokyo (JP)

( * ) Notice: Subject to any disclaimer, the term of this patent is extended or adjusted under 35 U.S.C. 154(b) by 0 days.

(21) Appl. No.: 15/774,390

(22) PCT Filed: Nov. 7, 2016

(86) PCT No.: PCT/JP2016/082957
§ 371 (c)(1),
(2) Date: Oct. 5, 2018

(87) PCT Pub. No.: WO2017/082202
PCT Pub. Date: May 18, 2017

(65) Prior Publication Data
US 2019/0022126 A1    Jan. 24, 2019

(30) Foreign Application Priority Data
Nov. 9, 2015  (JP) ................................ 2015-219183

(51) Int. Cl.
| | |
|---|---|
| *A61K 31/7105* | (2006.01) |
| *A61K 31/713* | (2006.01) |
| *C12N 15/113* | (2010.01) |
| *A61K 31/7088* | (2006.01) |
| *A61K 48/00* | (2006.01) |
| *A61K 31/4178* | (2006.01) |
| *A61K 31/4525* | (2006.01) |
| *C12Q 1/6883* | (2018.01) |
| *C12Q 1/70* | (2006.01) |
| *A61K 45/06* | (2006.01) |
| *C12Q 1/6886* | (2018.01) |
| *G01N 33/569* | (2006.01) |
| *A61P 31/20* | (2006.01) |

(52) U.S. Cl.
CPC ...... *A61K 31/7105* (2013.01); *A61K 31/4178* (2013.01); *A61K 31/4525* (2013.01); *A61K 31/7088* (2013.01); *A61K 31/713* (2013.01); *A61K 45/06* (2013.01); *A61K 48/00* (2013.01); *A61P 31/20* (2018.01); *C12N 15/113* (2013.01); *C12Q 1/6883* (2013.01); *C12Q 1/6886* (2013.01); *C12Q 1/706* (2013.01); *G01N 33/56983* (2013.01); *C12Q 2600/136* (2013.01); *C12Q 2600/158* (2013.01); *G01N 2500/02* (2013.01); *G01N 2500/04* (2013.01); *G01N 2500/10* (2013.01); *Y02A 50/385* (2018.01); *Y02A 50/387* (2018.01); *Y02A 50/389* (2018.01); *Y02A 50/391* (2018.01); *Y02A 50/393* (2018.01); *Y02A 50/463* (2018.01); *Y02A 50/465* (2018.01)

(58) Field of Classification Search
None
See application file for complete search history.

(56) References Cited

U.S. PATENT DOCUMENTS 7,008,776 B1 *  3/2006  Jaye ......................... C12N 9/18
                                                435/198

FOREIGN PATENT DOCUMENTS

| JP | 2015-2723 A | 1/2015 |
|---|---|---|
| WO | WO 02/090549 A2 | 11/2002 |
| WO | WO 2004/078181 A1 | 9/2004 |
| WO | WO 2010/080782 A2 | 7/2010 |
| WO | WO 2012/024170 A2 | 2/2012 |
| WO | WO 2014/094645 A1 | 6/2014 |
| WO | WO 2015/042420 A1 | 3/2015 |

OTHER PUBLICATIONS

Chen et al., "The Nedd4-like family of E3 ubiquitin ligases and cancer", Cancer Metastasis Rev., vol. 26, 2007, pp. 587-604.
European Search Report dated Jul. 26, 2019, for European Application No. 16864163.
Galinier et al., "Adenovirus Protein Involved in Virus Internalization Recruits Ubiquitin-Protein Ligases", Biochemistry, vol. 41, 2002, pp. 14299-14305.
International Search Report for International Application No. PCT/JP2016/082957, dated Feb. 7, 2017, with English translation.
Ishikawa, "Recent topics on hepatitis B", Kenko Bunka, vol. 47, Oct. 2012, pp. 1-6, with partial translation (Total 8 pages).
Miyazaki et al, "A novel HECT-type E3 ubiquitin ligase, NEDL2, stabilized p73 and enhances its transcriptional activity", Biochemical and Biophysical Research Communications, vol. 308, Jul. 3, 2003, pp. 106-113.

(Continued)

*Primary Examiner* — Tracy Vivlemore
(74) *Attorney, Agent, or Firm* — Birch, Stewart, Kolasch & Birch, LLP

(57) ABSTRACT

The present invention relates to an antiviral drug comprising as an active ingredient a substance capable of suppressing an expression of a target gene or an activity of a protein encoded by said target gene, wherein said target gene is one or more genes having an action of retaining virus-derived nucleic acid in a host cell and selected from the group consisting of DOCK11 gene, LIPG gene, DENND2A gene, and HECW2 gene. The present invention also relates to a screening method for the antiviral drug.

17 Claims, 10 Drawing Sheets
Specification includes a Sequence Listing.

(56) References Cited

OTHER PUBLICATIONS

Nakayama et al., Proceedings of the Japanese Society for Immunology, 2011, p. 219, Column of 3-G-W59-11-P, (Total 3 pages).
Nishikimi et al., "Zizimin2: a novel, DOCK180-related Cdc42 guanine nucleotide exchange factor expressed predominantly in lymphocytes", FEBS Letters, vol. 579, No. 5, 2005, pp. 1039-1046.
Seeger et al., "Molecular biology of hepatitis B virus infection", Virology, vol. 479-480, 2015, pp. 672-686.

\* cited by examiner

- pyrrole (Py)
- imidazole (Im)
- β-Alanin
- γ-aminobutyric acid
- N,N-dimethyl-1,3-propanediamine 1. CCGGCCAACAGGGTGCTTACATATTCTCGAGAATATGTAAGCACCCTGTTGGTTTTTG  6 sites
SEQ ID: No:1
              WCWWWW(B)
              WWCWWW(C)
              WWWCWW(D)
                WWWWCW(E)
                  WCWCGW(alpha)
        WCGWWW(beta)

2. CCGGGTACTAGACACCATATCATTTCTCGAGAAATGATATGGTGTCTAGTACTTTTTG  8 sites
SEQ ID: No:2
              WCWWWW(B)
              WWCWWW(C)
              WWWCWW(D)
              WWWWCW(E)
                WWWWCW(E)
        WCWCCW(N)
                  WCWCGW(alpha)
     WWGWCW(gamma)

3. CCGGACTAAATGAGCGGCTAATTAACTCGAGTTAATTAGCCGCTCATTTAGTTTTTTG  6 sites
SEQ ID: No:3    WWWWWW(A)
                WWWWWW(A)
        WCWWWW(B)
          WWWWGW(B)
                  WWWWCW(E)
                  WCWCGW(alpha)

4. CCGGTGATGGCCATAACCCATTAATCTCGAGATTAATGGGTTATGGCCATCATTTTTG  6 sites
SEQ ID: No:4    WWWWWW(A)
                WWWWCW(E)
              WCCCWW(L)
              WWCCCW(O)
        WGGCCW(S)
                  WCWCGW(alpha)

5. CCGGCCAGGCTACTTGAATCTGAATCTCGAGATTCAGATTCAAGTAGCCTGGTTTTTG  3 sites
SEQ ID: No:5  WWGWWW(D)
       WGGCWW(V)
                  WCWCGW(alpha)

FIG.19

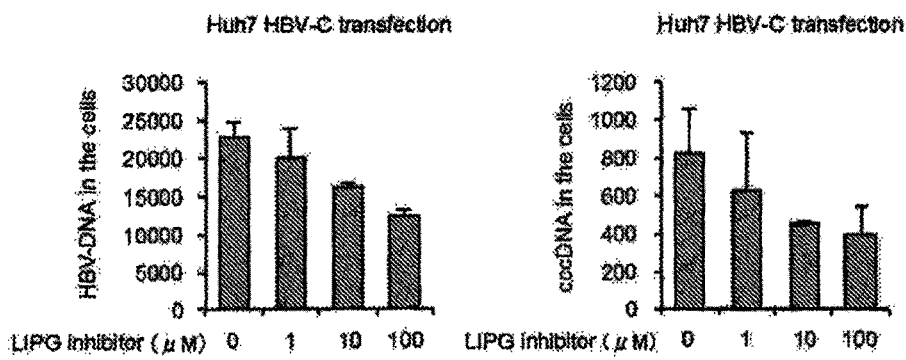

SEQUENCE LISTING

```
<160> NUMBER OF SEQ ID NOS: 64

<210> SEQ ID NO 1
<211> LENGTH: 58
<212> TYPE: DNA
<213> ORGANISM: Artificial Sequence
<220> FEATURE:
<223> OTHER INFORMATION: shRNA

<400> SEQUENCE: 1
ccggccaaca gggtgcttac atattctcga gaatatgtaa gcaccctgtt ggttttg          58

<210> SEQ ID NO 2
<211> LENGTH: 58
<212> TYPE: DNA
<213> ORGANISM: Artificial Sequence
<220> FEATURE:
<223> OTHER INFORMATION: shRNA

<400> SEQUENCE: 2
ccgggtacta gacaccatat catttctcga gaaatgatat ggtgtctagt acttttg          58

<210> SEQ ID NO 3
<211> LENGTH: 58
<212> TYPE: DNA
<213> ORGANISM: Artificial Sequence
<220> FEATURE:
<223> OTHER INFORMATION: shRNA

<400> SEQUENCE: 3
ccggactaaa tgagcggcta attaactcga gttaattagc cgctcattta gtttttg         58

<210> SEQ ID NO 4
<211> LENGTH: 58
<212> TYPE: DNA
<213> ORGANISM: Artificial Sequence
<220> FEATURE:
<223> OTHER INFORMATION: shRNA

<400> SEQUENCE: 4
```

```
<210> SEQ ID NO 5
<211> LENGTH: 58
<212> TYPE: DNA
<213> ORGANISM: Artificial Sequence
<220> FEATURE:
<223> OTHER INFORMATION: shRNA

<400> SEQUENCE: 5
ccggccaggc tacttgaatc tgaatctcga gattcagatt caagtagcct ggttttttg     58

<210> SEQ ID NO 6
<211> LENGTH: 59
<212> TYPE: DNA
<213> ORGANISM: Artificial Sequence
<220> FEATURE:
<223> OTHER INFORMATION: shRNA

<400> SEQUENCE: 6
ccggctgaag ggactaggca ataaactcga gtttattgcc tagtcccttc agttttttg     59

<210> SEQ ID NO 7
<211> LENGTH: 59
<212> TYPE: DNA
<213> ORGANISM: Artificial Sequence
<220> FEATURE:
<223> OTHER INFORMATION: shRNA

<400> SEQUENCE: 7
ccggccaatg aaggagaacc cttatctcga gataagggtt ctccttcatt ggttttttg     59

<210> SEQ ID NO 8
<211> LENGTH: 59
<212> TYPE: DNA
<213> ORGANISM: Artificial Sequence
<220> FEATURE:
<223> OTHER INFORMATION: shRNA

<400> SEQUENCE: 8
ccggcctagt gcagccctat tctttctcga gaaagaatag ggctgcacta ggttttttg     59

<210> SEQ ID NO 9
<211> LENGTH: 59
<212> TYPE: DNA
<213> ORGANISM: Artificial Sequence
<220> FEATURE:
<223> OTHER INFORMATION: shRNA

<400> SEQUENCE: 9
ccggctagtg cagccctatt ctttactcga gtaaagaata gggctgcact agttttttg     59

<210> SEQ ID NO 10
<211> LENGTH: 58
<212> TYPE: DNA
<213> ORGANISM: Artificial Sequence
<220> FEATURE:
<223> OTHER INFORMATION: shRNA

<400> SEQUENCE: 10
ccggacgatg tcttgggatc aattgctcga gcaattgatc ccaagacatc gttttttg      58

<210> SEQ ID NO 11
<211> LENGTH: 58
<212> TYPE: DNA
<213> ORGANISM: Artificial Sequence
```

<220> FEATURE:
<223> OTHER INFORMATION: shRNA

<400> SEQUENCE: 11
ccggatgcag gcaacttcgt gaaagctcga gctttcacga agttgcctgc attttttg    58

<210> SEQ ID NO 12
<211> LENGTH: 58
<212> TYPE: DNA
<213> ORGANISM: Artificial Sequence
<220> FEATURE:
<223> OTHER INFORMATION: shRNA

<400> SEQUENCE: 12
ccggccgttg taatagcatt ggctactcga gtagccaatg ctattacaac ggttttg    58

<210> SEQ ID NO 13
<211> LENGTH: 58
<212> TYPE: DNA
<213> ORGANISM: Artificial Sequence
<220> FEATURE:
<223> OTHER INFORMATION: shRNA

<400> SEQUENCE: 13
ccggcgtcac cctttatggc actaactcga gttagtgcca taagggtga cgttttg    58

<210> SEQ ID NO 14
<211> LENGTH: 58
<212> TYPE: DNA
<213> ORGANISM: Artificial Sequence
<220> FEATURE:
<223> OTHER INFORMATION: shRNA

<400> SEQUENCE: 14
ccggttacac ggatgcggtc aataactcga gttattgacc gcatccgtgt aattttg    58

<210> SEQ ID NO 15
<211> LENGTH: 57
<212> TYPE: DNA
<213> ORGANISM: Artificial Sequence
<220> FEATURE:
<223> OTHER INFORMATION: shRNA

<400> SEQUENCE: 15
ccgggcccaa acatttcttt gagatctcga gatctcaaag aaatgtttgg gcttttt    57

<210> SEQ ID NO 16
<211> LENGTH: 57
<212> TYPE: DNA
<213> ORGANISM: Artificial Sequence
<220> FEATURE:
<223> OTHER INFORMATION: shRNA

<400> SEQUENCE: 16
ccggccaggg aagttaaagt taattctcga gaattaactt taacttccct ggttttt    57

<210> SEQ ID NO 17
<211> LENGTH: 57
<212> TYPE: DNA
<213> ORGANISM: Artificial Sequence
<220> FEATURE:
<223> OTHER INFORMATION: shRNA

<400> SEQUENCE: 17
ccgggcacaa tacttggagt caattctcga gaattgactc caagtattgt gcttttt    57

<210> SEQ ID NO 18
<211> LENGTH: 57
<212> TYPE: DNA
<213> ORGANISM: Artificial Sequence
<220> FEATURE:
<223> OTHER INFORMATION: shRNA

<400> SEQUENCE: 18
ccgggcttac aatgacaaga ttgttctcga gaacaatctt gtcattgtaa gctttttt    57

<210> SEQ ID NO 19
<211> LENGTH: 57
<212> TYPE: DNA
<213> ORGANISM: Artificial Sequence
<220> FEATURE:
<223> OTHER INFORMATION: shRNA

<400> SEQUENCE: 19 ccggcccttta tcttaagatg tcaatctcga gattgacatc ttaagataag ggttttt    57

<210> SEQ ID NO 20
<211> LENGTH: 123
<212> TYPE: DNA
<213> ORGANISM: Artificial Sequence
<220> FEATURE:
<223> OTHER INFORMATION: Barcode linker
<220> FEATURE:
<221> NAME/KEY: misc_feature
<222> LOCATION: (62)..(73)
<223> OTHER INFORMATION: n is a, c, g, or t

<400> SEQUENCE: 20
ccatctcatc cctgcgtgtc tccgactcag gcagtgaaaa aaaaaaaaaa aaaaaaaaa    60 annnnnnnnn nnnacatagg ccgtcttcag ccgctgagac tgccaaggca cacaggggat   120
agg    123

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gctctgtatc gggaggcctt a    21

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
tgagtgctgt atggtgagga gaa    23

<210> SEQ ID NO 23
<211> LENGTH: 15
<212> TYPE: DNA
<213> ORGANISM: Artificial Sequence
<220> FEATURE:
<223> OTHER INFORMATION: Probe

<400> SEQUENCE: 23
agtctccgga acatt    15

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
accccaacaa ggatcattgg                                               20

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
cgaatgctcc cgctccta                                                 18

<210> SEQ ID NO 26
<211> LENGTH: 14
<212> TYPE: DNA
<213> ORGANISM: Artificial Sequence
<220> FEATURE:
<223> OTHER INFORMATION: Probe

<400> SEQUENCE: 26
cagaggcaaa tcag                                                     14

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgtcaacgac cgaccttgag                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cccaactcct cccagtcctt                                               20

<210> SEQ ID NO 29
<211> LENGTH: 22
<212> TYPE: DNA
<213> ORGANISM: Artificial Sequence
<220> FEATURE:
<223> OTHER INFORMATION: Probe

<400> SEQUENCE: 29
catacttcaa agactgtttg tt                                            22

<210> SEQ ID NO 30
<211> LENGTH: 20
<212> TYPE: DNA
<213> ORGANISM: Artificial Sequence
<220> FEATURE:

<223> OTHER INFORMATION: Primer

<400> SEQUENCE: 30
actcaccaac ctcctgtcct                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gacaaacggg caacatacct                                              20

<210> SEQ ID NO 32
<211> LENGTH: 24
<212> TYPE: DNA
<213> ORGANISM: Artificial Sequence
<220> FEATURE:
<223> OTHER INFORMATION: Probe

<400> SEQUENCE: 32
tatcgctgga tgtgtctgcg gcgt                                         24

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
cgtctgtgcc ttctcatctg c                                            21

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gcacagcttg gaggcttgaa                                              20

<210> SEQ ID NO 35
<211> LENGTH: 18
<212> TYPE: DNA
<213> ORGANISM: Artificial Sequence
<220> FEATURE:
<223> OTHER INFORMATION: Probe

<400> SEQUENCE: 35
ctgtaggcat aaattggt                                                18

<210> SEQ ID NO 36
<211> LENGTH: 21
<212> TYPE: DNA
<213> ORGANISM: Artificial Sequence
<220> FEATURE:
<223> OTHER INFORMATION: shRNA target sequence

<400> SEQUENCE: 36
ccaacagggt gcttacatat t                                            21

```
<210> SEQ ID NO 37
<211> LENGTH: 21
<212> TYPE: DNA
<213> ORGANISM: Artificial Sequence
<220> FEATURE:
<223> OTHER INFORMATION: shRNA target sequence

<400> SEQUENCE: 37
gtactagaca ccatatcatt t                                              21

<210> SEQ ID NO 38
<211> LENGTH: 21
<212> TYPE: DNA
<213> ORGANISM: Artificial Sequence
<220> FEATURE:
<223> OTHER INFORMATION: shRNA target sequence

<400> SEQUENCE: 38
actaaatgag cggctaatta a                                              21

<210> SEQ ID NO 39
<211> LENGTH: 21
<212> TYPE: DNA
<213> ORGANISM: Artificial Sequence
<220> FEATURE:
<223> OTHER INFORMATION: shRNA target sequence

<400> SEQUENCE: 39
tgatggccat aacccattaa t                                              21

<210> SEQ ID NO 40
<211> LENGTH: 21
<212> TYPE: DNA
<213> ORGANISM: Artificial Sequence
<220> FEATURE:
<223> OTHER INFORMATION: shRNA target sequence

<400> SEQUENCE: 40
ccaggctact tgaatctgaa t                                              21

<210> SEQ ID NO 41
<211> LENGTH: 21
<212> TYPE: DNA
<213> ORGANISM: Artificial Sequence
<220> FEATURE:
<223> OTHER INFORMATION: shRNA target sequence

<400> SEQUENCE: 41
ctgaagggac taggcaataa a                                              21

<210> SEQ ID NO 42
<211> LENGTH: 21
<212> TYPE: DNA
<213> ORGANISM: Artificial Sequence
<220> FEATURE:
<223> OTHER INFORMATION: shRNA target sequence

<400> SEQUENCE: 42
ccaatgaagg agaaccctta t                                              21

<210> SEQ ID NO 43
<211> LENGTH: 21
<212> TYPE: DNA
<213> ORGANISM: Artificial Sequence
<220> FEATURE:
<223> OTHER INFORMATION: shRNA target sequence
```

<400> SEQUENCE: 43
cctagtgcag ccctattctt t                                              21

<210> SEQ ID NO 44
<211> LENGTH: 21
<212> TYPE: DNA
<213> ORGANISM: Artificial Sequence
<220> FEATURE:
<223> OTHER INFORMATION: shRNA target sequence

<400> SEQUENCE: 44
ctagtgcagc cctattcttt a                                              21

<210> SEQ ID NO 45
<211> LENGTH: 21
<212> TYPE: DNA
<213> ORGANISM: Artificial Sequence
<220> FEATURE:
<223> OTHER INFORMATION: shRNA target sequence

<400> SEQUENCE: 45
acgatgtctt gggatcaatt g                                              21

<210> SEQ ID NO 46
<211> LENGTH: 21
<212> TYPE: DNA
<213> ORGANISM: Artificial Sequence
<220> FEATURE:
<223> OTHER INFORMATION: shRNA target sequence

<400> SEQUENCE: 46
atgcaggcaa cttcgtgaaa g                                              21

<210> SEQ ID NO 47
<211> LENGTH: 21
<212> TYPE: DNA
<213> ORGANISM: Artificial Sequence
<220> FEATURE:
<223> OTHER INFORMATION: shRNA target sequence

<400> SEQUENCE: 47
ccgttgtaat agcattggct a                                              21

<210> SEQ ID NO 48
<211> LENGTH: 21
<212> TYPE: DNA
<213> ORGANISM: Artificial Sequence
<220> FEATURE:
<223> OTHER INFORMATION: shRNA target sequence

<400> SEQUENCE: 48
cgtcacccct tatggcacta a                                              21

<210> SEQ ID NO 49
<211> LENGTH: 21
<212> TYPE: DNA
<213> ORGANISM: Artificial Sequence
<220> FEATURE:
<223> OTHER INFORMATION: shRNA target sequence

<400> SEQUENCE: 49
ttacacggat gcggtcaata a                                              21

<210> SEQ ID NO 50
<211> LENGTH: 21

```
<212> TYPE: DNA
<213> ORGANISM: Artificial Sequence
<220> FEATURE:
<223> OTHER INFORMATION: shRNA target sequence

<400> SEQUENCE: 50
gcccaaacat ttctttgaga t                                        21

<210> SEQ ID NO 51
<211> LENGTH: 21
<212> TYPE: DNA
<213> ORGANISM: Artificial Sequence
<220> FEATURE:
<223> OTHER INFORMATION: shRNA target sequence

<400> SEQUENCE: 51
ccagggaagt taaagttaat t                                        21

<210> SEQ ID NO 52
<211> LENGTH: 21
<212> TYPE: DNA
<213> ORGANISM: Artificial Sequence
<220> FEATURE:
<223> OTHER INFORMATION: shRNA target sequence

<400> SEQUENCE: 52
gcacaatact tggagtcaat t                                        21

<210> SEQ ID NO 53
<211> LENGTH: 21
<212> TYPE: DNA
<213> ORGANISM: Artificial Sequence
<220> FEATURE:
<223> OTHER INFORMATION: shRNA target sequence

<400> SEQUENCE: 53
gcttacaatg acaagattgt t                                        21

<210> SEQ ID NO 54
<211> LENGTH: 21
<212> TYPE: DNA
<213> ORGANISM: Artificial Sequence
<220> FEATURE:
<223> OTHER INFORMATION: shRNA target sequence

<400> SEQUENCE: 54
cccttatctt aagatgtcaa t                                        21

<210> SEQ ID NO 55
<211> LENGTH: 58
<212> TYPE: DNA
<213> ORGANISM: Artificial Sequence
<220> FEATURE:
<223> OTHER INFORMATION: shRNA

<400> SEQUENCE: 55
ccggccaaga acaaacagaa gcctactcga gtaggcttct gtttgttctt ggttttg     58

<210> SEQ ID NO 56
<211> LENGTH: 58
<212> TYPE: DNA
<213> ORGANISM: Artificial Sequence
<220> FEATURE:
<223> OTHER INFORMATION: shRNA

<400> SEQUENCE: 56
```
ccggcggaat atgtaccgac tgtttctcga gaaacagtcg gtacatattc cgttttg    58

<210> SEQ ID NO 57
<211> LENGTH: 58
<212> TYPE: DNA
<213> ORGANISM: Artificial Sequence
<220> FEATURE:
<223> OTHER INFORMATION: shRNA

<400> SEQUENCE: 57
ccggccctct actattgaga aacttctcga gaagtttctc aatagtagag ggttttg    58

<210> SEQ ID NO 58
<211> LENGTH: 58
<212> TYPE: DNA
<213> ORGANISM: Artificial Sequence
<220> FEATURE:
<223> OTHER INFORMATION: shRNA

<400> SEQUENCE: 58
ccggcagatg tatttctagt ctgttctcga gaacagacta gaaatacatc tgttttg    58

<210> SEQ ID NO 59
<211> LENGTH: 58
<212> TYPE: DNA
<213> ORGANISM: Artificial Sequence
<220> FEATURE:
<223> OTHER INFORMATION: shRNA

<400> SEQUENCE: 59
ccgggactct gtaacagact aattgctcga gcaattagtc tgttacagag tcttttg    58

<210> SEQ ID NO 60
<211> LENGTH: 21
<212> TYPE: DNA
<213> ORGANISM: Artificial Sequence
<220> FEATURE:
<223> OTHER INFORMATION: shRNA target sequence

<400> SEQUENCE: 60
ccaagaacaa acagaagcct a                                            21

<210> SEQ ID NO 61
<211> LENGTH: 21
<212> TYPE: DNA
<213> ORGANISM: Artificial Sequence
<220> FEATURE:
<223> OTHER INFORMATION: shRNA target sequence

<400> SEQUENCE: 61
cggaatatgt accgactgtt t                                            21

<210> SEQ ID NO 62
<211> LENGTH: 21
<212> TYPE: DNA
<213> ORGANISM: Artificial Sequence
<220> FEATURE:
<223> OTHER INFORMATION: shRNA target sequence

<400> SEQUENCE: 62
ccctctacta ttgagaaact t                                            21

<210> SEQ ID NO 63
<211> LENGTH: 21
<212> TYPE: DNA
<213> ORGANISM: Artificial Sequence -continued

```
<220> FEATURE:
<223> OTHER INFORMATION: shRNA target sequence

<400> SEQUENCE: 63
cagatgtatt tctagtctgt t                                          21

<210> SEQ ID NO 64
<211> LENGTH: 21
<212> TYPE: DNA
<213> ORGANISM: Artificial Sequence
<220> FEATURE:
<223> OTHER INFORMATION: shRNA target sequence

<400> SEQUENCE: 64
gactctgtaa cagactaatt g                                          21
```

ANTIVIRAL DRUGS

TECHNICAL FIELD

The present invention relates to a novel antiviral drug.

The present application claims the priority to Japanese Patent Application No. 2015-219183, which is incorporated herein by reference.

BACKGROUND ART

Diseases associated with viral infection, such as viral hepatitis, influenza infection, herpesviral infection, AIDS, and viral hemorrhagic fever, are recognized as medically and socially important problems. For the diseases associated with viral infection, preventions using vaccines and the like, and therapies using drugs, for example, are widely studied. However, it cannot be said that such vaccines and drugs produce sufficient effects, and furthermore elucidation of their action mechanisms per se may be difficult in some viruses so that development of drugs against such viruses still cannot be started. In addition, since traits of viruses are extremely diverse and transcription factors etc. involved in their life cycles are also varied, the development of drugs is currently underway for individual viruses.

Hepatitis B virus (hereinafter abbreviated as "HBV"), one of the causes of diseases associated with virus infection, is thought to affect more than 350 million people worldwide. HBV causes acute or chronic hepatitis after infection, and some of the hepatitis cases further progress to hepatic cirrhosis or hepatic cancer. Currently, interferons (IFNs) and nucleotide analogs are used in the treatment of hepatitis B caused by HBV. However, it is difficult to completely eliminate the virus even in patients receiving long-term administration of such agents, and furthermore, there are problems with the agents, such as occurrence of resistant viruses and acute exacerbations in patients receiving long-term administration, increase in severity due to re-exacerbation after completion of administration, and the like.

After HBV enters a hepatocyte, the viral genes move into the nucleus of the hepatocyte, and then converted from incompletely circular double-stranded DNA into Hepatitis B virus covalently closed circular DNA (HBV cccDNA). It is known that HBV cccDNA is bare closed circular HBV DNA that is present in the nucleus of hepatocytes and acts as a replicative intermediate during viral replication (Non-Patent Document 1). In hepatocytes, HBV cccDNA behaves in the same manner as the human genome and stays in the nucleus. It is also known that HBV cccDNA is not directly affected by an antiviral nucleotide analog and still remains in hepatocytes after nucleotide analog therapy. It is a clinical fact that HBV viral genome cannot be completely eliminated from hepatocytes with existing agents, and therefore radical cure of HBV infection is thought to be impossible (Non-Patent Document 2).

Since HBV cccDNA has the property of staying within the cell after HBV infection, it has attracted attention in recent years as a marker for prediction of long-term prognosis for antiviral drugs and degree of liver damage. However, the in vivo mechanism of retaining HBV after infection has not yet been elucidated, and also the behavior of HBV cccDNA remains unclear. As a drug focusing on HBV cccDNA, an artificial DNA nuclease targeting HBV cccDNA itself has been reported (Patent Document 1).

For complete removal of HBV from hepatocytes to prevent or treat hepatitis B, there is a great need for elucidating HBV retention mechanism including behavior of cccDNA and thereby discovering a new molecule(s) that can be a target of anti-HBV drug.

PRIOR ART DOCUMENT(S)

Patent Document(s)

Patent Document 1: JP 2015-002723 A

Non-Patent Document(S)

Non-Patent Document 1: Christoph Seeger, William S. Mason, Virology 479-480 (2015) 672.686

Non-Patent Document 2: Tetsuya Ishikawa, "Recent topics on hepatitis B", Kenko Bunka No. 47 (published in October 2012) (http://www.kenkobunkajp/kenbun/kb47.html)

SUMMARY OF THE INVENTION

Problems to be Solved by the Invention

An object of the present invention is to provide a novel antiviral drug.

Means for Solving the Problems

As a result of intensive studies, the present inventors focused on the facts that the DOCK11. LIPG, DENND2A and HECW2 genes are expressed specifically in HBV mRNA-positive hepatocytes, and that suppression of the expression of these genes decreases the amount of HBV cccDNA in hepatocytes, and that these genes may be involved in the infection and proliferation mechanisms of the viruses in general, to find that substances capable of suppressing the expression or activity of the proteins encoded by these genes can be used as antiviral drugs, thereby accomplishing the present invention.

That is, the present invention is as follows:

1. An antiviral drug comprising as an active ingredient a substance capable of suppressing an expression of a target gene or an activity of a protein encoded by said target gene, wherein said target gene is one or more genes having an action of retaining virus-derived nucleic acid in a host cell and selected from the group consisting of DOCK11 gene, LIPG gene, DENND2A gene, and HECW2 gene.
2. The antiviral drug according to 1 mentioned above, wherein the target gene is DOCK11 gene.
3. The antiviral drug according to 1 or 2 mentioned above, wherein the substance capable of suppressing the expression of the target gene or the activity of the protein encoded by the target gene is one or more compounds selected from the group consisting of shRNA, siRNA, miRNA, antisense oligonucleotide, and pyrrole-imidazole polyamide for the target gene or transcription product thereof.
4. The antiviral drug according to any one of 1 to 3 mentioned above, wherein the substance capable of suppressing the expression of the target gene or the activity of the protein encoded by the target gene recognizes a base sequence selected from any of the followings:

```
                                         (SEQ ID NO: 36)
CCAACAGGGTGCTTACATATT (SEQ ID NO: 37)
GTACTAGACACCATATCATTT
```

```
                                    (SEQ ID NO: 38)
ACTAAATGAGCGGCTAATTAA (SEQ ID NO: 39)
TGATGGCCATAACCCATTAAT (SEQ ID NO: 40)
CCAGGCTACTTGAATCTGAAT (SEQ ID NO: 41)
CTGAAGGGACTAGGCAATAAA (SEQ ID NO: 42)
CCAATGAAGGAGAACCCTTAT (SEQ ID NO: 43)
CCTAGTGCAGCCCTATTCTTT (SEQ ID NO: 44)
CTAGTGCAGCCCTATTCTTTA (SEQ ID NO: 45)
ACGATGTCTTGGGATCAATTG (SEQ ID NO: 46)
ATGCAGGCAACTTCGTGAAAG (SEQ ID NO: 47)
CCGTTGTAATAGCATTGGCTA (SEQ ID NO: 48)
CGTCACCCTTTATGGCACTAA (SEQ ID NO: 49)
TTACACGGATGCGGTCAATAA (SEQ ID NO: 50)
GCCCAAACATTTCTTTGAGAT (SEQ ID NO: 51)
CCAGGGAAGTTAAAGTTAATT (SEQ ID NO: 52)
GCACAATACTTGGAGTCAATT (SEQ ID NO: 53)
GCTTACAATGACAAGATTGTT (SEQ ID NO: 54)
CCCTTATCTTAAGATGTCAAT
``` a base sequence obtained by substituting, deleting, adding and/or inserting one to several bases in any one of the base sequences of the above-described SEQ ID NOs: 36 to 54.

5. The antiviral drug according to any one of 1 to 4 mentioned above, wherein the substance capable of suppressing the expression of the target gene or the activity of the protein encoded by the target gene is an shRNA comprising a base sequence selected from any of the followings:

```
                                    (SEQ ID NO: 1)
CCGGCCAACAGGGTGCTTACATATTCTCGAGAATATGTAAGCACCCTGT
TGGTTTTTG (SEQ ID NO: 2)
CCGGGTACTAGACACCATATCATTTCTCGAGAAATGATATGGTGTCTAG
TACTTTTTG (SEQ ID NO: 3)
CCGGACTAAATGAGCGGCTAATTAACTCGAGTTAATTAGCCGCTCATTT
AGTTTTTG (SEQ ID NO: 4)
CCGGTGATGGCCATAACCCATTAATCTCGAGATTAATGGGTTATGGCCA
TCATTTTTG (SEQ ID NO: 5)
CCGGCCAGGCTACTTGAATCTGAATCTCGAGATTCAGATTCAAGTAGCC
TGGTTTTTG (SEQ ID NO: 6)
CCGGCTGAAGGGACTAGGCAATAAACTCGAGTTTATTGCCTAGTCCCTT
CAGTTTTTG (SEQ ID NO: 7)
CCGGCCAATGAAGGAGAACCCTTATCTCGAGATAAGGGTTCTCCTTCAT
TGGTTTTTG (SEQ ID NO: 8)
CCGGCCTAGTGCAGCCCTATTCTTTCTCGAGAAAGAATAGGGCTGCACT
AGGTTTTTG (SEQ ID NO: 9)
CCGGCTAGTGCAGCCCTATTCTTTACTCGAGTAAAGAATAGGGCTGCAC
TAGTTTTTG (SEQ ID NO: 10)
CCGGACGATGTCTTGGGATCAATTGCTCGAGCAATTGATCCCAAGACAT
CGTTTTTG (SEQ ID NO: 11)
CCGGATGCAGGCAACTTCGTGAAAGCTCGAGCTTTCACGAAGTTGCCT
GCATTTTTG (SEQ ID NO: 12)
CCGGCCGTTGTAATAGCATTGGCTACTCGAGTAGCCAATGCTATTACAA
CGGTTTTG (SEQ ID NO: 13)
CCGGCGTCACCCTTTATGGCACTAACTCGAGTTAGTGCCATAAAGGGTG
ACGTTTTG (SEQ ID NO: 14)
CCGGTTACACGGATGCGGTCAATAACTCGAGTTATTGACCGCATCCGTG
TAATTTTG (SEQ ID NO: 15)
CCGGGCCCAAACATTTCTTTGAGATCTCGAGATCTCAAAGAAATGTTTG
GGCTTTTT (SEQ ID NO: 16)
CCGGCCAGGGAAGTTAAAGTTAATTCTCGAGAATTAACTTTAACTTCCC
TGGTTTTT (SEQ ID NO: 17)
CCGGGCACAATACTTGGAGTCAATTCTCGAGAATTGACTCCAAGTATTG
TGCTTTTT (SEQ ID NO: 18)
CCGGGCTTACAATGACAAGATTGTTCTCGAGAACAATCTTGTCATTGTA
AGCTTTTT (SEQ ID NO: 19)
CCGGCCCTTATCTTAAGATGTCAATCTCGAGATTGACATCTTAAGATAA
GGGTTTTT
``` a base sequence obtained by substituting, deleting, adding and/or inserting one to several bases in any one of the base sequences of the above-described SEQ ID NOs: 1 to 19.

6. The antiviral drug according to any one of 1 to 5 mentioned above, wherein the virus is selected from hepatitis B virus, hepatitis C virus, hepatitis A virus, hepatitis E virus, influenza virus, human immunodeficiency virus, RS virus, papillomavirus, adenovirus, poliovirus, echovirus, coxsackievirus, enterovirus, rhinovirus, rotavirus, norovirus, Newcastle disease virus, mumps virus, vesicular stomatitis virus, rabies virus, Lassa virus, measles virus, rubella virus, filovirus, Ebola virus, Japanese encephalitis virus, yellow fever virus, dengue virus, West Nile virus, and Zika virus.

7. The antiviral drug according to any one of 1 to 6 mentioned above, wherein the virus is hepatitis virus.

8. The antiviral drug according to any one of 1 to 7 mentioned above, wherein the virus is hepatitis B virus.

9. The antiviral drug according to any one of 1 to 8 mentioned above, which is used in combination with a viral growth inhibitor.

10. A pharmaceutical composition for treatment and/or prevention of a disease associated with viral infection, which contains the antiviral drug according to any one of 1 to 9 mentioned above.

11. A screening method for an antiviral drug, comprising selecting, as an antiviral drug, a substance capable of suppressing an expression of a target gene or an activity of a protein encoded by said target gene from test substances, wherein said target gene is one or more genes having an action of retaining virus-derived nucleic acid in a host cell and selected from the group consisting of DOCK11 gene, LIPG gene, DENND2A gene, and HECW2 gene.

12. The screening method for an antiviral drug according to 11 mentioned above, the method comprising the following steps (A) to (C) of:
(A) bringing a cell into contact with a test substance in a system in which the cell expresses the target gene;
(B) measuring the expression level of the target gene in the cell and comparing the expression level of the target gene in the cell contacted with the test substance to the expression level of the target gene in the cell not contacted with the test substance;
(C) selecting a test substance that causes a decrease in the expression level of the target gene in the cell as an antiviral drug through screening based on the comparison result in step (B) above.

13. The screening method for an antiviral drug according to 11 mentioned above, the method comprising the following steps (a) to (c) of:
(a) bringing a protein encoded by the target gene into contact with a protein that interacts with the protein encoded by the target gene in the presence of a test substance;
(b) measuring the binding ability between the protein encoded by the target gene and the protein that interacts with the protein encoded by the target gene, and comparing the binding ability in the presence of the test substance to the binding ability in the absence of the test substance;
(c) selecting a test substance that causes a decrease in the binding ability between the protein encoded by the target gene and the protein that interacts with the protein encoded by the target gene as an antiviral drug based on the comparison result in step (b) above.

14. The screening method for an antiviral drug according to 11 mentioned above, the method comprising the following steps (a) to (c) of:
(a) bringing a protein encoded by the target gene into contact with a substrate for the protein encoded by the target gene in the presence of a test substance;
(b) measuring the enzymatic activity of the protein encoded by the target gene, and comparing the enzymatic activity in the presence of the test substance to the enzymatic activity in the absence of the test substance;
(c) selecting a test substance that causes a decrease in the enzymatic activity of the protein encoded by the target gene as an antiviral drug based on the comparison result in step (b) above.

15. An antiviral drug, which is selected through screening by the screening method for an antiviral drug according to any one of 11 to 14 mentioned above.

16. A method of detecting a gene having an action of retaining virus-derived nucleic acid in a host cell, the method comprising analyzing a host cell after viral infection for the expression patterns of two or more finite numbers of genes, and detecting the gene having an action of retaining virus-derived nucleic acid in the host cell from host cell-derived genes.

17. The method of detecting a gene having an action of retaining virus-derived nucleic acid in a host cell according to 16 mentioned above, the method comprising the following steps:
(1) establishing a virus-positive cell line from virus-positive tissue specimen collected from a single organism;
(2) subculturing the virus-positive cell line to prepare a virus-positive cell(s) and a virus-negative cell(s);
(3) analyzing the virus-positive cell(s) and virus-negative cell(s) obtained in the step (2) for the expression patterns of two or more finite numbers of genes in each single cell;
(4) comparing the expression pattern of the genes in the virus-positive cell(s) to the expression pattern of the genes in the virus-negative cell(s);
(5) selecting a gene showing a higher expression level in the virus-positive cell(s) as compared to the virus-negative cell(s) as the gene having an action of retaining virus-derived nucleic acid in the host cell.

18. The method of detecting a gene having an action of retaining virus-derived nucleic acid in a host cell according to 17 mentioned above, wherein the virus expresses a transcription product comprising poly A at its 3' end from a virus-derived gene; and wherein by the analysis of the expression patterns of the genes in the step (3), a cell expressing the virus-derived gene is identified as virus-positive cell, and a cell not expressing the virus-derived gene is identified as virus-negative cell.

19. The method of detecting a gene having an action of retaining virus-derived nucleic acid in a host cell according to 18 mentioned above, wherein the virus is hepatitis B virus; and wherein the gene having an action of retaining virus-derived nucleic acid in a host cell is a gene having an action of retaining hepatitis B virus-derived cccDNA in a host cell.

20. A gene having an action of retaining virus-derived nucleic acid in a host cell, which is selected by the method of selecting a gene having an action of retaining virus-derived nucleic acid in a host cell according to any one of 16 to 19 mentioned above.

21. A gene derived from a host cell and having an action of retaining hepatitis B virus-derived cccDNA in a host cell.

22. The gene according to 20 or 21 mentioned above, which is one or more genes having an action of retaining virus-derived nucleic acid in a host cell selected from DOCK11 gene, LIPG gene, DENND2A gene, and HECW2 gene.

23. An antiviral drug comprising as an active ingredient a substance capable of suppressing an expression of a target gene or an activity of a protein encoded by said target gene, wherein said target gene is a gene having an action of retaining virus-derived nucleic acid in a host cell according to any one of 20 to 22 mentioned above.

24. A screening method for an antiviral drug, comprising selecting, as an antiviral drug, a substance capable of suppressing an expression of a target gene or an activity of a protein encoded by said target gene from test substances, wherein said target gene is a gene having an action of retaining virus-derived nucleic acid in a host cell according to any one of 20 to 22 mentioned above.

A) An antiviral drug that targets a gene having an action of retaining virus-derived nucleic acid in a host cell, and comprises as an active ingredient a substance capable of suppressing an expression of the target gene or an activity of a protein encoded by the target gene, wherein the target gene is Cdc42 gene.

B) The antiviral drug according to A) above, wherein the substance capable of suppressing the expression of the target gene or the activity of the protein encoded by the target gene recognizes the base sequence selected from any of the followings:

CCAAGAACAAACAGAAGCCTA (SEQ ID NO: 60)

CGGAATATGTACCGACTGTTT (SEQ ID NO: 61)

CCCTCTACTATTGAGAAACTT (SEQ ID NO: 62)

CAGATGTATTTCTAGTCTGTT (SEQ ID NO: 63)

GACTCTGTAACAGACTAATTG (SEQ ID NO: 64)

a base sequence obtained by substituting, deleting, adding and/or inserting one to several (preferably 5 or less, more preferably 2 or less) bases in any one of the base sequences of the above-described SEQ ID NOs: 60 to 64.

C) The antiviral drug according to A) or B) above, wherein the substance capable of suppressing the expression of the target gene or the activity of the protein encoded by the target gene is an shRNA comprising the base sequence selected from any of the followings:

CCGGCCAAGAACAAACAGAAGCCTACTCGAGTAGGCTTCTGTTTGTTCTTGGTTTTTG (SEQ ID NO: 55)

CCGGCGGAATATGTACCGACTGTTTCTCGAGAAACAGTCGGTACATATTCCGTTTTTG (SEQ ID NO: 56)

CCGGCCCTCTACTATTGAGAAACTTCTCGAGAAGTTTCTCAATAGTAGAGGGTTTTTG (SEQ ID NO: 57)

CCGGCAGATGTATTTCTAGTCTGTTCTCGAGAACAGACTAGAAATACATCTGTTTTTG (SEQ ID NO: 58)

CCGGGACTCTGTAACAGACTAATTGCTCGAGCAATTAGTCTGTTACAGAGTCTTTTTG (SEQ ID NO: 59)

a base sequence obtained by substituting, deleting, adding and/or inserting one to several (preferably 5 or less, more preferably 2 or less) bases in any one of the base sequences of the above-described SEQ ID NOs: 55 to 59.

D) A pharmaceutical composition for treatment and/or prevention of a disease associated with viral infection, which contains the antiviral drug according to any one of A) to C) above.

E) A screening method for an antiviral drug, comprising selecting, as an antiviral drug, a substance capable of suppressing an expression of a target gene or an activity of a protein encoded by said target gene from test substances, wherein said target gene is one or more genes having an action of retaining virus-derived nucleic acid in a host cell and selected from the group consisting of CD42 gene.

Effect of the Invention

The antiviral drug of the present invention is thought to have a different mechanism of action from conventional antiviral drugs and act on the transport pathway to the nuclei after virus enters across the membrane on the surface of host cells. Therefore, it is contemplated that the antiviral drug of the present invention exhibits an antiviral effect not only on HBV but on various viruses. Further, it is contemplated that the antiviral drug of the present invention exerts an antiviral effect synergistically in combination with a conventional antiviral drug. Furthermore, by using the target gene of the present invention as an indicator, screening for an antiviral drug based on a novel mechanism can be achieved.

The antiviral drug of the present invention can greatly reduce the amount of HBV cccDNA in hepatocytes, for example, compared to conventional growth inhibitors for hepatitis B virus, and can also completely remove it. In addition, the antiviral drug of the present invention can be used in combination with a conventional growth inhibitor for hepatitis B virus to synergistically remove HBV cccDNA and prevent the reactivation of HBV. Therefore, it is contemplated that the antiviral drug of the present invention can contribute to complete cure of HBV infection.

BRIEF DESCRIPTION OF THE DRAWINGS

FIG. 19 exemplifies pyrrole-imidazole polyamides which can act as a substance capable of suppressing the expression or activity of the protein encoded by the target gene of the present invention.

FIG. 20 shows the effects of treatment with an LIPG inhibitor on the amount of HBV DNA and the amount of HBV cccDNA, which were investigated using an HBV infection system in human hepatocytes. (Example 10)

MODE FOR CARRYING OUT THE INVENTION

Figure 1:
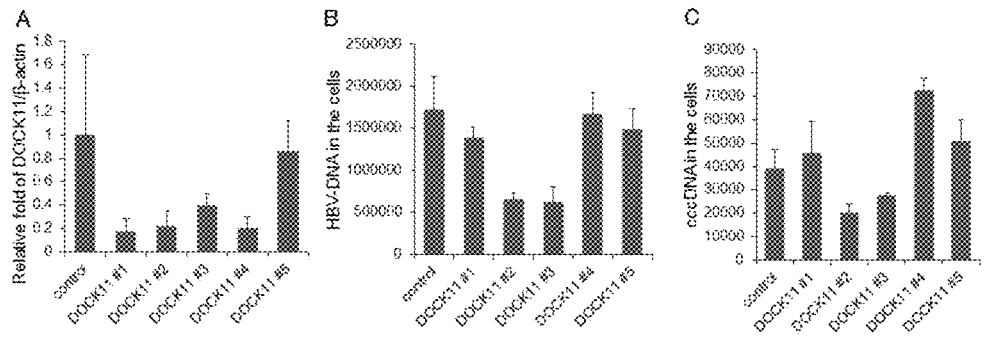
FIG. 1 shows the results of investigation of the effects of various shRNAs against DOCK11 gene introduced into HBV-infected hepatoma cells on: the expression level of DOCK11 gene (A); the amount of HBV DNA (B); and the amount of HBV cccDNA (C). In the panel (A), the expression levels are expressed as relative values by taking the control level as 1. (Example 2)
Figure 2:
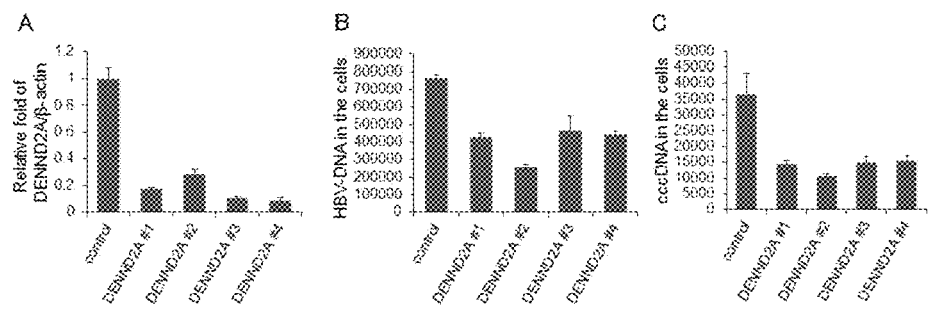
FIG. 2 shows the results of investigation of the effects of various shRNAs against DENND2A introduced into HBV-infected hepatoma cells on: the expression level of DENND2A gene (A); the amount of HBV DNA (B); and the amount of HBV cccDNA (C). In the panel (A), the expression levels are expressed as relative values by taking the control level as 1. (Example 2)
Figure 3:
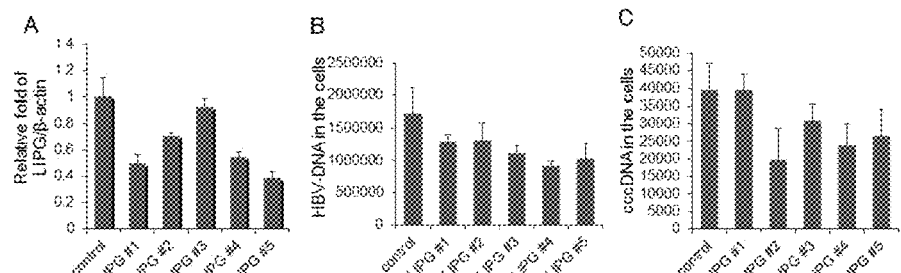
FIG. 3 shows the results of investigation of the effects of various shRNAs against LIPG gene introduced into HBV-infected hepatoma cells on: the expression level of LIPG gene (A); the amount of HBV DNA (B); and the amount of HBV cccDNA (C). In the panel (A), the expression levels are expressed as relative values by taking the control level as 1. (Example 2)
Figure 4:
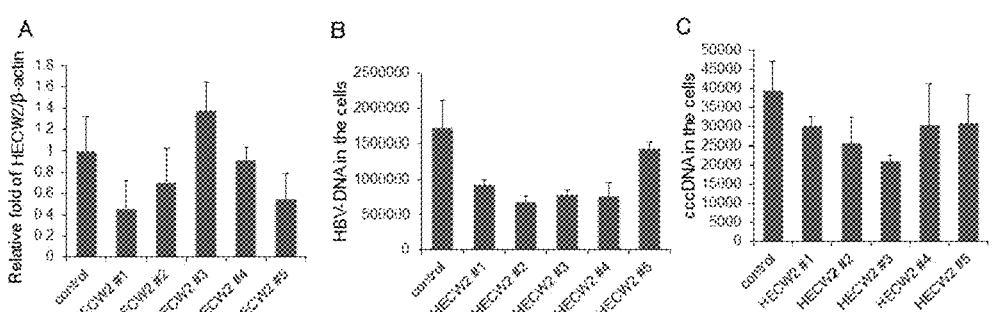
FIG. 4 shows the results of investigation of the effects of various shRNAs against HECW2 gene introduced into HBV-infected hepatoma cells on: the expression level of HECW2 gene (A); the amount of HBV DNA (B); and the amount of HBV cccDNA (C). In the panel (A), the expression levels are expressed as relative values by taking the control level as 1. (Example 2)
Figure 5:
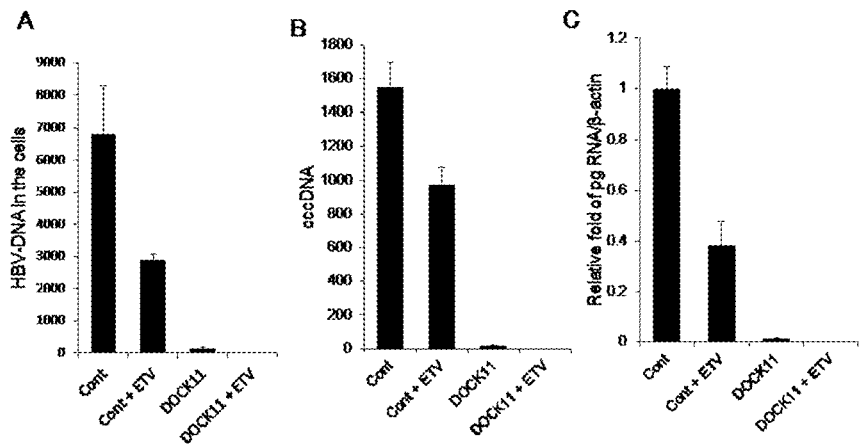
FIG. 5 shows the effects of introduction of an shRNA against DOCK11 gene on: the amount of HBV DNA (A); the amount of HBV cccDNA (B); and the expression level of pregenomic RNA (hereinafter simply referred to as "pg RNA," which is also referred to as "preg RNA") (C), which were investigated using an HBV infection system in human hepatocytes. In the panel (C), the expression levels are expressed as relative values by taking the control level as 1. (Example 3)
Figure 6:
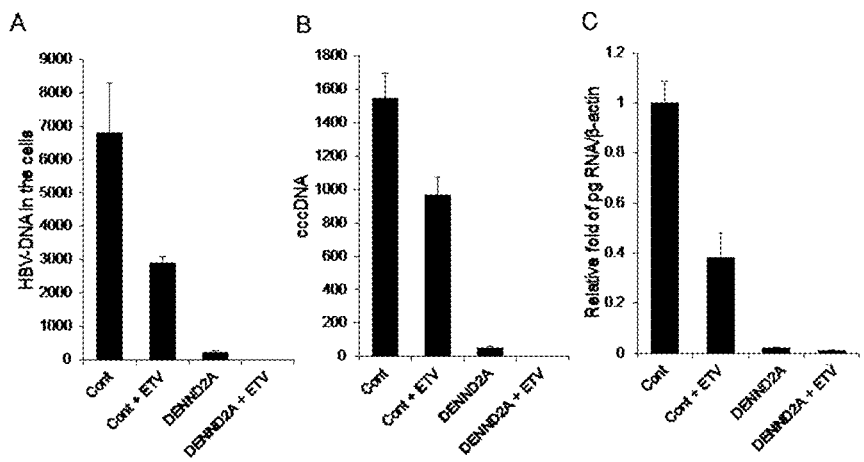
FIG. 6 shows the effects of introduction of an shRNA against DENND2A gene on: the amount of HBV DNA (A); the amount of HBV cccDNA (B); and the expression level of pg RNA (C), which were investigated using an HBV infection system in human hepatocytes. In the panel (C), the expression levels are expressed as relative values by taking the control level as 1. (Example 3)
Figure 7:
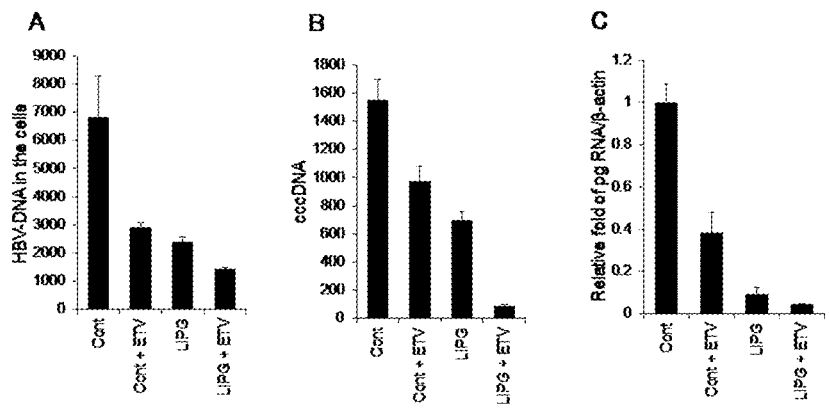
FIG. 7 shows the effects of introduction of an shRNA against LIPG gene on: the amount of HBV DNA (A); the amount of HBV cccDNA (B); and the expression level of pg RNA (C), which were investigated using an HBV infection system in human hepatocytes. In the panel (C), the expression levels are expressed as relative values by taking the control level as 1. (Example 3)
Figure 8:
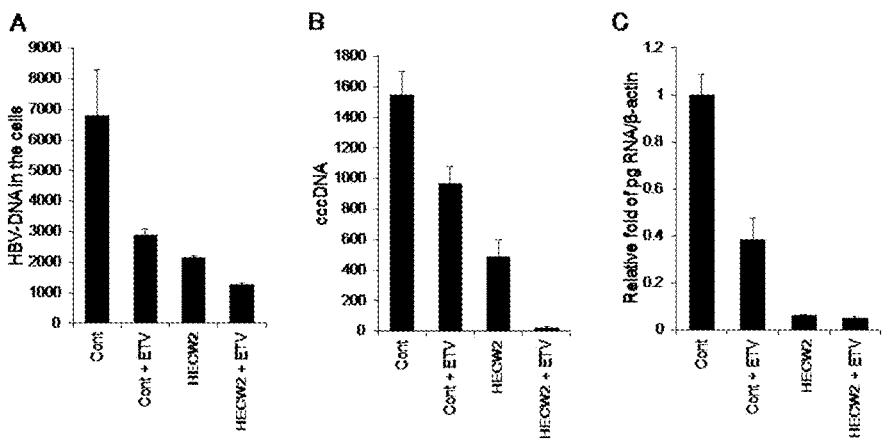
FIG. 8 shows the effects of introduction of an shRNA against HECW2 gene on: the amount of HBV DNA (A); the amount of HBV cccDNA (B); and the expression level of pg RNA (C), which were investigated using an HBV infection system in human hepatocytes. In the panel (C), the expression levels are expressed as relative values by taking the control level as 1. (Example 3)
Figure 9:
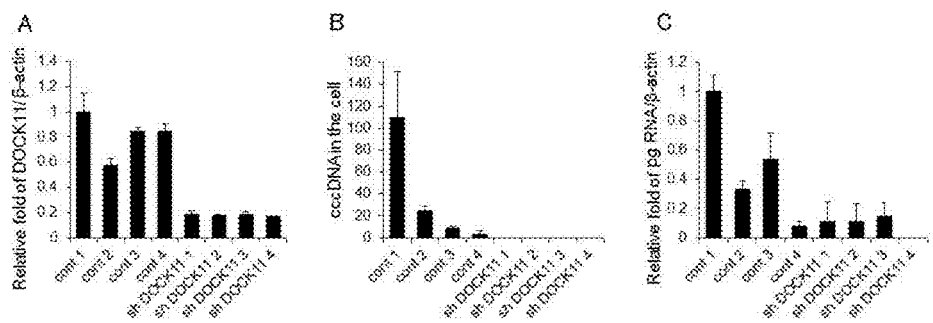
FIG. 9 shows the effects of introduction of an shRNA against DOCK11 gene on: the expression level of DOCK11 gene (A); the amount of HBV cccDNA (B); and the expression level of pgRNA (C), which were investigated using an HBV infection system in human hepatocytes, in which the hepatocytes were long-term cultured after the shRNA introduction. In the panels (A) and (C), the expression levels are expressed as relative values by taking the level in the hepatocytes infected with HBV (cont 1) in each panel as 1. (Example 4)
Figure 10:
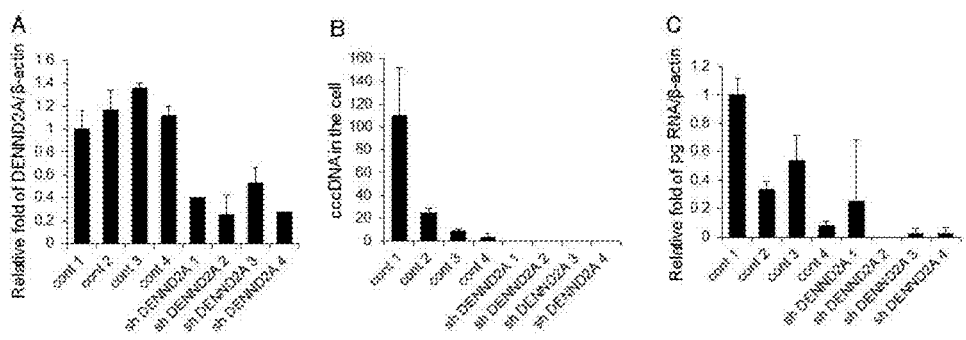
FIG. 10 shows the effects of introduction of an shRNA against DENND2A gene on: the expression level of DENND2A gene (A); the amount of HBV cccDNA (B); and the expression level of pg RNA (C), which were investigated using an HBV infection system in human hepatocytes, in which the hepatocytes were long-term cultured after the shRNA introduction. In the panels (A) and (C), the expression levels are expressed as relative values by taking the level in the hepatocytes infected with HBV (cont 1) in each panel as 1. (Example 4)
Figure 11:
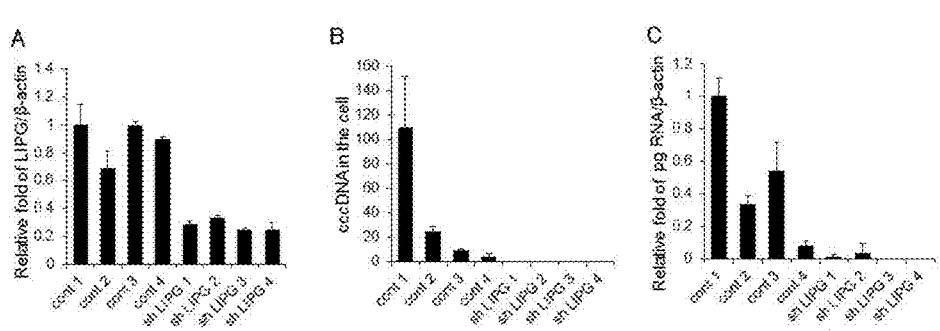
FIG. 11 shows the effects of introduction of an shRNA against LIPG gene on: the expression level of LIPG gene (A); the amount of HBV cccDNA (B); and the expression level of pg RNA (C), which were investigated using an HBV infection system in human hepatocytes, in which the hepatocytes were long-term cultured after the shRNA introduction. In the panels (A) and (C), the expression levels are expressed as relative values by taking the level in the hepatocytes infected with HBV (cont 1) in each panel as 1. (Example 4)
Figure 12:
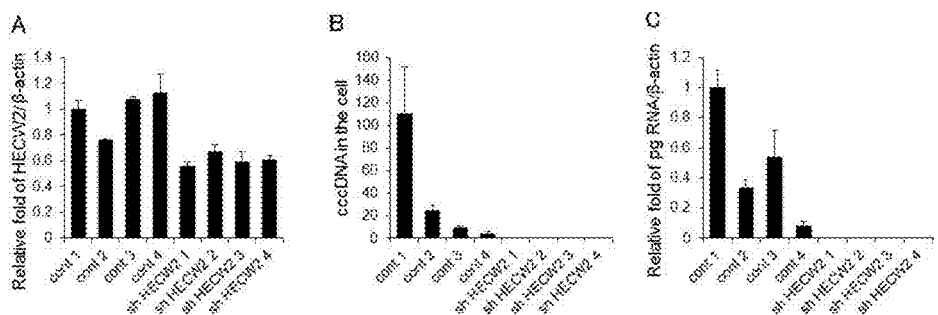
FIG. 12 shows the effects of introduction of an shRNA against HECW2 gene on: the expression level of HECW2 gene (A); the amount of HBV cccDNA (B); and the expression level of pg RNA (C), which were investigated using an HBV infection system in human hepatocytes, in which the hepatocytes were long-term cultured after the shRNA introduction. In the panels (A) and (C), the expression levels are expressed as relative values by taking the level in the hepatocytes infected with HBV (cont 1) in each panel as 1. (Example 4)

First, the background of the completion of the present invention will be described below.

The present inventors have surprisingly confirmed that some cells in a human hepatocellular carcinoma (HCC) cell line established from a hepatitis B-positive patient with hepatocellular carcinoma expressed HBV mRNA. Cultured cells expressing HBV mRNA established so far have been prepared by transient infection with HBV of limited kinds of cells that HBV can infect, and there are no cell models which enables persistent infection. Thus, it has not been thought that cells expressing HBV mRNA could be established as a cell line from living bodies. In the cell line confirmed by the present inventors, although the number of HBV mRNA positive cells is decreased by passage, a few cells showing positivity for HBV mRNA still remain after subculturing. The present inventors thought that a mechanism for retaining HBV mRNA could be working in these HBV mRNA positive cells, and that investigation of the HBV mRNA positive cells could lead to identification of the gene involved in the retention of HBV mRNA. As a result of analyzing human hepatocellular carcinoma cells established from a hepatitis B-positive patient with hepatocellular carcinoma using the comprehensive single-cell gene expression analysis method established by the present inventors (PCT/JP2015/60841), it was confirmed that only one cell among approximately 3,000 cells expressed HBV mRNA and that this HBV mRNA positive cell highly expressed DENND2A, LIPG, Dock11 and HECW2 genes as compared to other cells. In addition, by introducing shRNA capable of suppressing the expression of these target genes into HBV-infected cells, the amounts of HBV DNA and HBV cccDNA dramatically decreased. Furthermore, the shRNA against each of the genes in combination with entecavir synergistically reduced the amounts of HBV DNA and cccDNA. Of particular note are that combined use of shRNA for DENND2A gene or Dock11 gene with entecavir reduced the amount of cccDNA to a level below the detection limit in short-term culture, and that in long-term culture over 3 weeks, each of the four genes reduced the amount of cccDNA to a level below the detection limit when used alone. These results indicate the possibility that the LIPG, HECW2, DENND2A and Dock11 genes have an important function for retaining the latency of HBV in cells, and it was thought that substances that suppress these genes or their proteins could become new anti-HBV drugs.

Since the target genes in the present invention encode proteins such as a protein involved in cytoskeleton or a protein which interacts with the Rab family functioning as a membrane organizer, it is predicted that the target genes in the present invention will become target genes for antiviral drugs not only against HBV but against viruses in general. Examples of the viruses include HCV and influenza virus as shown in the Examples. Thus, a drug which acts on the target gene in the present invention can be selected as an antiviral drug through screening. The drug acting on the target gene is one having an action of suppressing the expression of the target gene or the activity of the protein encoded by the target gene. Suppression of the expression of the target gene means inhibition of the process in which the target gene expresses a protein it encodes. Since the protein encoded by the target gene in the present invention is thought to affect a specific enzyme activity, screening for a drug acting on the target gene can be easily performed by measuring the enzyme activity. For example, since LIPG has an enzyme activity, screening for a drug acting on the LIPG gene can be easily performed by measuring the enzyme activity.

The antiviral drug of the present invention is a drug targeting a gene having an action of retaining virus-derived nucleic acid in a host cell, and containing, as an active ingredient, a substance capable of suppressing the expression of the target gene or the activity of the protein encoded by the target gene. The target gene is preferably one or more genes selected from the group consisting of DOCK11 gene, LIPG gene, DENND2A gene, and HECW2 gene. The gene having an action of retaining virus-derived nucleic acid in a host cell is not a gene derived from viral genome, but a gene derived from the host cell genome. It is thought that factors of some sort in the host cell are involved in the retention of the virus in the host cell, in addition to the activity and function of the virus itself. The antiviral drug of the present invention targets such a factor(s) of some sort in a host cell.

The antiviral drug of the present invention has an antiviral action. The antiviral action means an action of suppressing or inhibiting, for example, viral infection, replication, particle production and reinfection. In particular, the antiviral drug of the present invention exerts its effects to decrease the amount of viral DNA in host cells. For example, from the fact that the antiviral drug of the present invention exerts an effect of decreasing the amount of HBV DNA, particularly the amount of HBV cccDNA, in hepatocytes when used as an anti-HBV drug, it is thought that the drug affects the uptake of incomplete circular double-stranded DNA of HBV into the nucleus of the hepatocytes and the stability of cccDNA in the nucleus. There is no report on antiviral drugs that can exert the effect of decreasing the amount of viral DNA by targeting genes in host cells. There is also no report on anti-HBV drugs that can exert the effect of decreasing the amount of cccDNA in nucleus by targeting genes in hepatocytes. The antiviral drug of the present invention exerts its antiviral action via a novel mechanism. Since the antiviral drug of the present invention is based on a novel mechanism, it can be used in combination with other viral growth inhibitors to remove viruses more effectively. For example, entecavir, a conventional hepatitis B virus growth inhibitor, inhibits production of HBV particles by inhibiting reverse transcription to minus-strand DNA which occurs after transcription from cccDNA to mRNA and subsequent core particle generation. When the antiviral drug of the present invention is used as an anti-HBV drug, it can be used in combination with (an)other growth inhibitor(s) for hepatitis B virus such as entecavir to remove HBV more effectively.

In the life cycle of HBV, HBV first interacts with heparan sulfate proteoglycan (HSPG) on the liver cell surface and binds to the cell surface to enter the cell by endocytosis. It is known that NTCP (sodium taurocholate cotransporting polypeptide) present on the basolateral side of liver cells acts as a receptor for HBV entry. For HBV infection, there are NTCP-dependent and -independent systems. After HBV entry into cells, the membrane of HBV fuses to the endosomal membrane following the maturation of endosomes (vesicles), to release nucleocapsids composed of viral genome and capsid packaging the genome into the cytoplasm. It is believed that the nucleocapsids are transported within the cell using cytoskeletal microtubules and enter the nucleus through interaction with motor proteins. On reaching nuclear pore complexes, nucleocapsids send HBV DNA and HBV polymerase into the nucleus. Within the nucleus, the relaxed circular DNA (rcDNA) is converted into cccDNA, which then serves as a template for transcription (Journal of Gastroenterology and Hepatology, 31: 302-309 (2016). Doi: 10.1111/jgh. 13175). The mechanism is thought to be common to all viruses, in which, after the virus entry into a host cell, the virus genome is transported within the cell by means of cytoskeleton such as microtubule and enters the nucleus. Since the proteins encoded by the target genes in the present invention relate to cytoskeleton, it is believed that the antiviral drug of the present invention acts on the transport of virus from the cell membrane into the nucleus and exerts the effect not only on HBV but on various viruses.

The application of the antiviral drug of the present invention includes in vivo and ex vivo uses, and the aspect of in vivo use will be described later as a "pharmaceutical composition for treatment and/or prevention." The antiviral drug of the present invention can be administered to any animal that viruses can infect. For example, the antiviral drug can be administered to human and non-human mammals such as monkey, mouse, rat, dog, rabbit, cattle and horse, and in particular, it is preferably administered to human.

Viruses targeted by the antiviral drug of the present invention may be any virus. Examples of the virus include hepatitis B virus, hepatitis C virus, hepatitis A virus, hepatitis E virus, influenza virus, human immunodeficiency virus, RS virus, papillomavirus, adenovirus, poliovirus, echovirus, coxsackievirus, enterovirus, rhinovirus, rotavirus, norovirus, Newcastle disease virus, mumps virus, vesicular stomatitis virus, rabies virus, Lassa virus, measles virus, rubella virus, Filovirus, Ebola virus, Japanese encephalitis virus, yellow fever virus, dengue virus, West Nile virus, and Zika virus. Among them, preferred is hepatitis viruses including hepatitis B virus, hepatitis C virus, hepatitis A virus and hepatitis E virus, and influenza virus, human immunodeficiency virus, Ebola virus, and Zika virus; more preferred is hepatitis viruses; still more preferred is hepatitis B virus or hepatitis C virus; and most preferred is hepatitis B virus.

DOCK 11 (dedicator of cytokinesis 11) is a gene having the base sequence shown in GenBank Accession No. NM_144658. The DOCK11 gene is a member of the Dock family and is thought to have a function as a guanyl nucleotide exchange factor targeting the Rho GTPase family. The function of the DOCK11 gene can be confirmed by measuring the activity of the target Rho GTPase. The Rho GTPase family is known to have an action of controlling the cytoskeleton. DOCK11 is also known to interact with Cdc42, and it is also possible to use the action and the phenotype of Cdc42 as an indicator. (J. Chem. Biol., 281: 35253-35262 (2006) & J. Chem. Biol., 286: 25341-25351 (2011))

DENND2A (DENN/MADD domain containing 2A) gene has the base sequence shown in GenBank Accession No. NM_144658. The DENND2A gene encodes a protein containing a DENN/MADD domain at its C-terminal side, and is thought to have a function as a guanyl nucleotide exchange factor which specifically acts on Rab. The function of the DENND2A gene can also be confirmed by using the function of Rab, which is a target of this gene, as an indicator. Rab is a small G-protein belonging to the Ras superfamily. Small G-proteins belonging to the Ras superfamily are known to regulate transport pathways in a cell and are thought to be involved in, for example, vesicle formation, migration of vesicles and organelles, and binding of vesicles to targets (Nature Reviews Molecular Cell Biology, 2, 107-117 (2001)).

LIPG (lipase, endothelial) gene has the base sequence shown in GenBank Accession No. NM 006033. It is known that vascular endothelial lipase encoded by the LIPG gene is an enzyme that hydroxylates HDL and other lipoproteins and widely distributed in the body.

HECW2 (HECT, C2 and WW domain containing E3 ubiquitin protein ligase 2) gene has the base sequence shown in GenBank Accession No. NM_020760. The HECW2 gene is also referred to as NEDL2 gene. The protein encoded by the HECW2 gene has a ligase activity and is thought to act as a ubiquitin transferase.

The antiviral drug of the present invention can comprise as an active ingredient one or more substances capable of suppressing the expression of the target gene or the activity of the protein encoded by the target gene. The active ingredient is not particularly limited as long as it can suppress the expression of the target gene or the activity of the protein encoded by the target gene. The phrase "suppressing the expression of the target gene or the activity of the protein encoded by the target gene" is synonymous with suppressing the expression or activity of the protein encoded by the target gene. The phrase "suppressing the expression or activity of the protein" refers to any aspect in which the functional expression of the protein is suppressed (or inhibited), and includes, but is not limited to, suppressing the activity (function) of the protein, and suppressing the expression of the protein (e.g. suppression of gene expression, including suppression of the transcription of the gene encoding the protein and suppression of the translation to the protein). Aspects in which the activity of the protein is suppressed include, but are not limited to, inhibition of the binding between a protein receptor and a ligand or an associating molecule, inhibition of the interaction between intracellular proteins, inhibition of the activation of the protein, and inhibition of the enzymatic activity of the protein. The antiviral drug of the present invention may be a drug that inhibits the interaction between the protein encoded by the target gene and a specific gene or a molecule such as a protein. The specific gene or protein or the like may be one which has been revealed to interact with the protein encoded by the target gene, or may be one which will be confirmed to interact with it in the future.

Examples of the active ingredient of the antiviral drug of the present invention include, but are not limited to, inhibitors of the protein encoded by the target gene; antibodies that specifically bind to the protein encoded by the target gene; compounds capable of suppressing the expression of the protein encoded by the target gene; and association inhibitors in cases where the protein acts in association with its target protein(s).

As the above-described inhibitor of the protein encoded by the target gene, any inhibitors for the protein encoded by the target gene which are already known or will be developed in future can be used. Preferably, the above-described inhibitor is an inhibitor specific for the protein encoded by the target gene.

As the above-described antibody that specifically binds to the protein encoded by the target gene, any antibodies capable of inhibiting the function of the protein encoded by the target gene, which are already known or will be developed in future, can be used. For example, antibodies that bind to the active site of the protein encoded by the target gene and inhibit its function are included. Such antibodies may be polyclonal or monoclonal. Both polyclonal antibodies and monoclonal antibodies can be appropriately prepared by methods known to those skilled in the art. When the antibodies are monoclonal, they may be chimeric antibodies, humanized antibodies, or human antibodies prepared by known methods. The antibodies may also be, for example, but are not limited to, complete antibody molecules, antibody fragments, bispecific antibodies, minibodies, domain antibodies, synthetic antibodies (also referred to as "antibody mimetics"), antibody fusions (also referred to as "antibody conjugates"), or fragments thereof. Antibody fragments include Fab fragments, Fd fragments, Fv fragments, dAb fragments, CDR regions, F(ab')2 fragments, single chain Fvs (ScFvs), minibodies, diabodies, triabodies, and tetrabodies.

Examples of the compounds capable of suppressing the expression of the protein encoded by the target gene include nucleic acids, proteins, polyamides, and the like which can suppress the expression of the protein encoded by the target gene. Such nucleic acids, proteins, polyamides and the like may be those that can suppress the expression or activity of the protein encoded by the target gene via recognition of a base sequence selected from any of the followings:

```
CCAACAGGGTGCTTACATATT              (SEQ ID NO: 36)

GTACTAGACACCATATCATTT              (SEQ ID NO: 37)

ACTAAATGAGCGGCTAATTAA              (SEQ ID NO: 38)

TGATGGCCATAACCCATTAAT              (SEQ ID NO: 39)

CCAGGCTACTTGAATCTGAAT              (SEQ ID NO: 40)

CTGAAGGGACTAGGCAATAAA              (SEQ ID NO: 41)

CCAATGAAGGAGAACCCTTAT              (SEQ ID NO: 42)

CCTAGTGCAGCCCTATTCTTT              (SEQ ID NO: 43)

CTAGTGCAGCCCTATTCTTTA              (SEQ ID NO: 44)

ACGATGTCTTGGGATCAATTG              (SEQ ID NO: 45)

ATGCAGGCAACTTCGTGAAAG              (SEQ ID NO: 46)

CCGTTGTAATAGCATTGGCTA              (SEQ ID NO: 47)

CGTCACCCTTTATGGCACTAA              (SEQ ID NO: 48)

TTACACGGATGCGGTCAATAA              (SEQ ID NO: 49)

GCCCAAACATTTCTTTGAGAT              (SEQ ID NO: 50)

CCAGGGAAGTTAAAGTTAATT              (SEQ ID NO: 51)

GCACAATACTTGGAGTCAATT              (SEQ ID NO: 52)

GCTTACAATGACAAGATTGTT              (SEQ ID NO: 53)

CCCTTATCTTAAGATGTCAAT              (SEQ ID NO: 54)
``` a base sequence obtained by substituting, deleting, adding and/or inserting one to several (preferably 5 or less, more preferably 2 or less) bases in any one of the base sequences of the above-described SEQ ID NOs: 36 to 54.

The above-described nucleic acid capable of suppressing the expression of the protein encoded by the target gene include, but not limited to, RNA molecules having an RNA interference action (action considered to be based on specifically destroying mRNA derived from the target gene) such as antisense oligonucleotides, shRNAs, siRNAs, and dsRNAs against the target gene or the transcription product thereof; and miRNAs and aptamers considered to be capable of suppressing the translation of the mRNA of the target gene. The antisense oligonucleotide is a single stranded DNA or RNA molecule complementary to the target sequence, and binds to the complementary DNA or RNA to inhibit its expression.

The RNA molecules having an RNA interference action can be appropriately designed by a person skilled in the art by using a known method based on the information about the base sequence of the target gene. The RNA molecule can be prepared by a person skilled in the art according to a known method, and those which are distributed in the market can be obtained and used. As the above-described nucleic acid capable of suppressing the expression of the protein encoded by the target gene, siRNA, shRNA and miRNA are preferable, and siRNA and shRNA are particularly preferable. The nucleic acids capable of suppressing the expression of the protein encoded by the target gene which can be used include, but are not limited to, those having an activity of inhibiting transcription or translation of the gene described above.

The above-described nucleic acid capable of suppressing the expression of the protein encoded by the target gene is a nucleic acid that binds to a portion of the target gene and suppresses the expression of the protein. The RNA or DNA molecule capable of binding to a portion of the target gene can be introduced into a cell by a method known per se.

The above-described RNA or DNA molecules can be introduced into a cell by using a DNA molecule, such as a vector, capable of expressing these molecules, and the vector can be appropriately prepared by a person skilled in the art by a known method. Specific examples of the vectors include, but are not limited to, adenoviral vectors, lentiviral vectors, and adeno-associated viral vectors. Preferably, the vector is a lentiviral vector.

As the nucleic acid capable of suppressing the expression of the protein encoded by the target gene of the present invention, one or more nucleic acids selected from the nucleic acids having the nucleotide sequences listed below can be used:

(DOCK11 gene)
```
                                               (SEQ ID NO: 1)
CCGGCCAACAGGGTGCTTACATATTCTCGAGAATATGTAAGCACCCTGT
TGGTTTTTG (SEQ ID NO: 2)
CCGGGTACTAGACACCATATCATTTCTCGAGAAATGATATGGTGTCTAG
TACTTTTTG (SEQ ID NO: 3)
CCGGACTAAATGAGCGGCTAATTAACTCGAGTTAATTAGCCGCTCATTT
AGTTTTTTG (SEQ ID NO: 4)
CCGGTGATGGCCATAACCCATTAATCTCGAGATTAATGGGTTATGGCCA
TCATTTTTG
```

-continued (DENND2A gene)

(SEQ ID NO: 5)
CCGGCCAGGCTACTTGAATCTGAATCTCGAGATTCAGATTCAAGTAGCC
TGGTTTTTG (SEQ ID NO: 6)
CCGGCTGAAGGGACTAGGCAATAAACTCGAGTTTATTGCCTAGTCCCTT
CAGTTTTTG (SEQ ID NO: 7)
CCGGCCAATGAAGGAGAACCCTTATCTCGAGATAAGGGTTCTCCTTCAT
TGGTTTTTG (SEQ ID NO: 8)
CCGGCCTAGTGCAGCCCTATTCTTTCTCGAGAAAGAATAGGGCTGCACT
AGGTTTTTG (SEQ ID NO: 9)
CCGGCTAGTGCAGCCCTATTCTTTACTCGAGTAAAGAATAGGGCTGCAC
TAGTTTTTG (LIPG gene)

(SEQ ID NO: 10)
CCGGACGATGTCTTGGGATCAATTGCTCGAGCAATTGATCCCAAGACAT
CGTTTTTG (SEQ ID NO: 11)
CCGGATGCAGGCAACTTCGTGAAAGCTCGAGCTTTCACGAAGTTGCCT
GCATTTTTG (SEQ ID NO: 12)
CCGGCCGTTGTAATAGCATTGGCTACTCGAGTAGCCAATGCTATTACAA
CGGTTTTTG (SEQ ID NO: 13)
CCGGCGTCACCCTTTATGGCACTAACTCGAGTTAGTGCCATAAAGGGTG
ACGTTTTTG (SEQ ID NO: 14)
CCGGTTACACGGATGCGGTCAATAACTCGAGTTATTGACCGCATCCGTG
TAATTTTTG (HECW2 gene)

(SEQ ID NO: 15)
CCGGGCCCAAACATTTCTTTGAGATCTCGAGATCTCAAAGAAATGTTTG
GGCTTTTT (SEQ ID NO: 16)
CCGGCCAGGGAAGTTAAAGTTAATTCTCGAGAATTAACTTTAACTTCCC
TGGTTTTT (SEQ ID NO: 17)
CCGGGCACAATACTTGGAGTCAATTCTCGAGAATTGACTCCAAGTATTG
TGCTTTTT (SEQ ID NO: 18)
CCGGGCTTACAATGACAAGATTGTTCTCGAGAACAATCTTGTCATTGTA
AGCTTTTT (SEQ ID NO: 19)
CCGGCCCTTATCTTAAGATGTCAATCTCGAGATTGACATCTTAAGATAA
GGGTTTTT a base sequence that is obtained by substituting, deleting, adding and/or inserting one to several (preferably 5 or less, more preferably 2 or less) bases in any one of the base sequences of the above-described SEQ ID NOs: 1 to 19 and exerts RNA interference action on each gene.

In each shRNA, the terminal CCGG and TTTTTG or TTTTT are regions to be cleaved by a Dicer, and CTCGAG constitutes a hairpin loop structure. The base sequence between CCGG and CTCGAG corresponds to the target sense strand, and the base sequence between CTCGAG and TTTTTG or TTTTT corresponds to the antisense strand. Accordingly, the underlined base sequences in the sense strands correspond to the cleavage sites in the target gene, which are the base sequences of the portions of the target gene to which each shRNA can bind or the complementary sequence thereof. The nucleic acids capable of suppressing the expression of the protein encoded by the target gene which can be used in the present invention are not limited to the nucleic acids having the base sequence shown in SEQ ID NOs: 1 to 19, and may be nucleic acids that can bind to the underlined nucleotide sequences and/or the complementary sequences thereof and suppress the expression of the protein encoded by the target gene. The nucleic acids may comprise substitution, deletion, addition and/or insertion of one to several (preferably 5 or less, more preferably 2 or less) bases in each of the underlined portions, as long as such nucleic acids exert an RNA interference action on each gene.

As a polyamide capable of suppressing the expression of the protein encoded by the target gene, DNA-binding pyrrole-imidazole polyamides (PIP) have been known. Pyrrole-imidazole polyamides are a group of synthetic compounds and composed of pyrrole-imidazole polyamide comprising an N-methyl pyrrole unit (hereinafter also referred to as "Py") and an N-methyl imidazole unit (hereinafter also referred to as "Im"), which are aromatic rings, and a γ-aminobutyric acid unit (Dervan: Bioorg Med Chem. 2001; 9: 2215-35). PIP can be synthesized by sequentially coupling Py and Im, and can be folded in the presence of γ-aminobutyric acid into a U-shaped conformation. The Py, Im, and γ-aminobutyric acid unit (also referred to as "γ linker") are connected to each other via an amide bond (—C(=O)—NH—), and the general structure and the production method are known (JP3045706B, JP2001-136974A, WO03/000683A1, JP2009-120531A). PIP can be conveniently produced by an automated synthesis method based on a known solid phase method using Fmoc (9-fluorenyl-methoxycarbonyl) (solid phase Fmoc method). According to the known Fmoc method or the like, PIP having a carboxyl group at the terminal can be synthesized. Specific examples thereof include PIPs having a β-alanine residue (β-amino-propionic acid residue) and a γ-aminobutyric acid residue at the terminal.

PIP can bind with high affinity and specificity to a specific base pair in minor grooves in a double helical DNA. The specific recognition of base pairs is dependent on a one-to-one pairing between Py and Im. That is, in the U-shaped conformation in minor grooves of DNA, the Py/Im pair targets C-G base pairs, Im/Py targets G-C base pairs, and Py/Py targets both A-T and T-A base pairs (Dervan: Bioorg Med Chem. 2001; 9: 2215-35.). Since PIP can specifically inhibit a gene expression, it has no side effects. Furthermore, since PIP is a low molecular weight compound, it does not have the drawback of being degraded by ribonuclease. Since PIP can permeate into cell nuclei without using reagents for introduction or vectors and bind to a specific base pair with high affinity and specificity to suppress the expression of a specific gene, it is expected as a novel gene transcription regulator.

Figure 18:
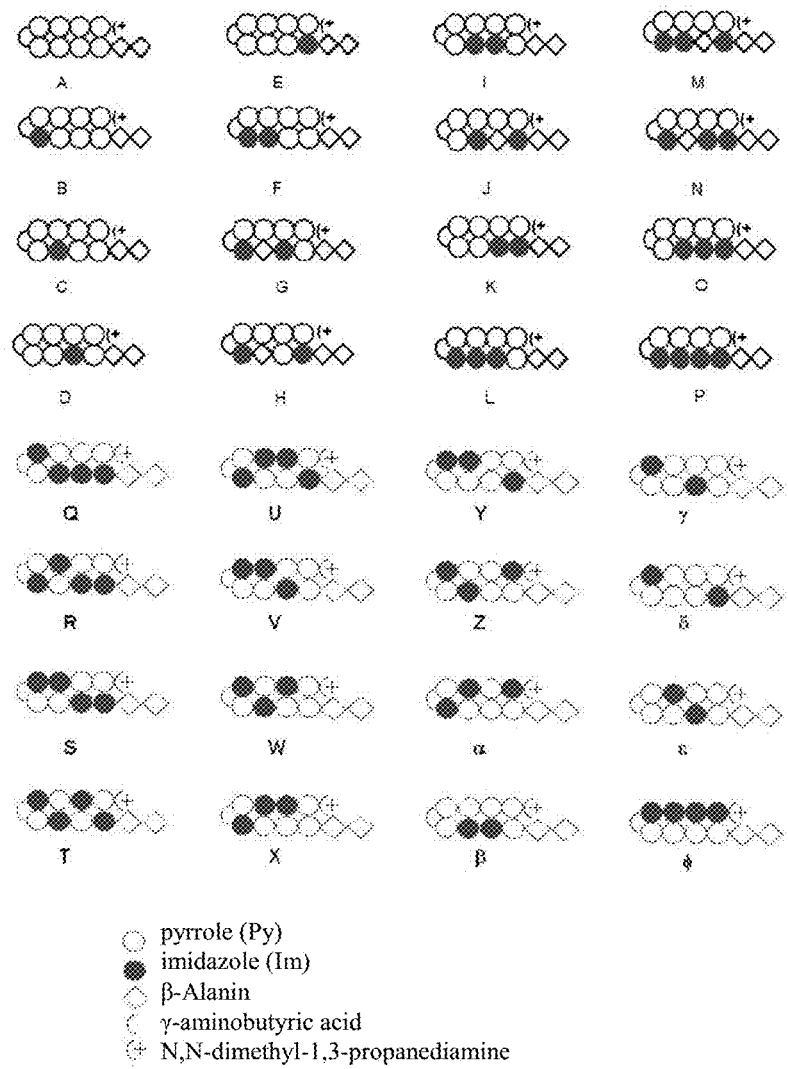
FIG. 18 depicts a diagram showing a library of pyrrole-imidazole polyamides which bind to DNA in a sequence-selective manner.

As a library of PIPs, (A) to (Z) and (α) to (φ) shown in FIG. 18 are known (Pandian G N, et al., Sci Rep. 2014 Jan. 24; 4:3843. doi: 10.1038/srep03843). Among the PIPs shown in FIG. 18, the structural formula of (B) (O-ββAc, Chemical Formula: $C_{62}H_{78}N_{24}O_{12}$, Exact Mass: 1350.62, Molecular Weight: 1351.46, ChemBioChem 2014, 15, 2647-2651) is exemplified below.

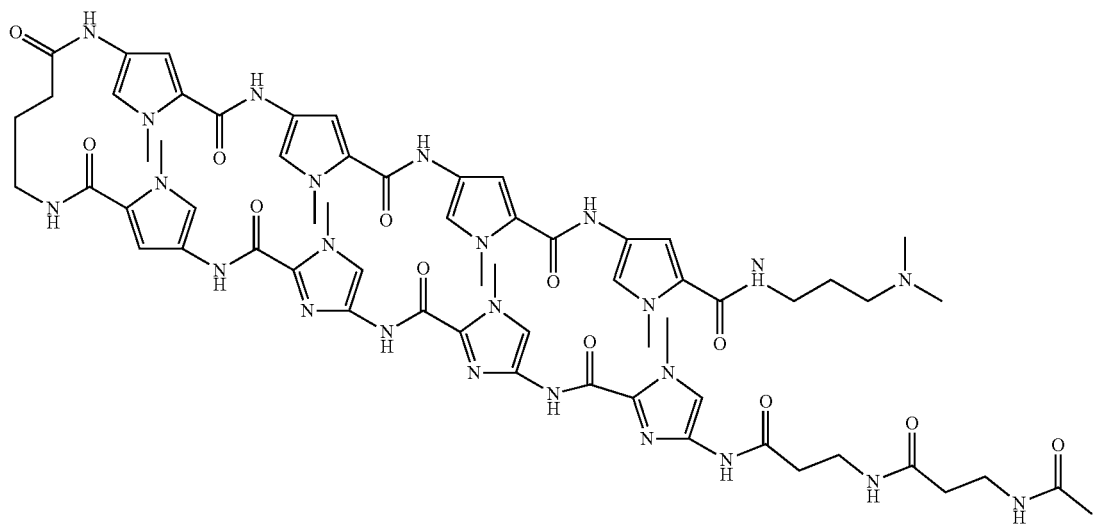 [SMILES: CC(=O)NCCC(=O)NCCC(=O)Nc1cn(C)c(C(=O)Nc2cn(C)c(C(=O)Nc3cn(C)c(C(=O)Nc4cc(C(=O)NCCCC(=O)Nc5cc(C(=O)Nc6cc(C(=O)Nc7cc(C(=O)Nc8cc(C(=O)NCCCN(C)C)n(C)c8)n(C)c7)n(C)c6)n(C)c5)n(C)c4)n3)n2)n1]

An important point of gene regulation is transcription. Binding of transcription factors to the gene promoter region initiates the transcription, which results in syntheses of transcription products, followed by translation based on the synthesized transcription products. The PIP capable of suppressing the transcription of the target gene of the present invention can be selected from the library shown in FIG. 18. Examples of the base sequence to which PIP binds include the base sequence of the gene promoter region necessary for initiating transcription of the target gene, the base sequences shown in SEQ ID NOs: 36 to 54, or a base sequence obtained by substituting, deleting, adding and/or inserting one to several bases in any one of the base sequences of the above-described SEQ ID NOs: 36 to 54. As shown in FIG. 19, it is preferable to use PIPs (γ) and (B) shown in FIG. 18 for the base sequence shown in SEQ ID NO: 37. It is preferable to use PIPs (B) and (A) for the base sequence shown in SEQ ID NO: 38. It is preferable to use PIPs (S) and (A) for the base sequence shown in SEQ ID NO: 39. In FIG. 19, W indicates A-T base pair recognition.

The antiviral drug of the present invention may be provided as a pharmaceutical composition which contains the said antiviral drug and is for treatment and/or prevention of diseases associated with viral infection. Examples of the diseases associated with viral infection include hepatitis B, hepatitis C, influenza, AIDS, Ebola hemorrhagic fever, and Zika fever. The pharmaceutical composition can be formulated according to a known technique. Specific examples of the formulations include, but are not limited to, solid formulations such as tablets, capsules, pills, powders, and granules, and liquid formulations such as solutions, suspensions, emulsions and injections. Depending on the form of the formulation, pharmaceutically acceptable carriers and additives can be added as appropriate. Specific examples of the carriers and additives include, but are not limited to, preservatives, stabilizers, excipients, fillers, binders, wetting agents, flavoring agents, and coloring agents. When the formulation is a liquid formulation, a known pharmaceutically acceptable solvent such as a physiologic saline or a solution having a buffering action can be used.

The dose of the pharmaceutical composition of the present invention is not particularly limited as long as it can produce an antiviral effect of the active ingredient, and can be appropriately set by a person skilled in the art. The dose of the active ingredient can be, for example, 0.01 to 1000 mg, preferably 0.05 to 500 mg, more preferably 0.1 to 100 mg per kg body weight of patient per dose.

The method for administering the pharmaceutical composition of the present invention is not particularly limited as long as it can produce the antiviral effect, and can be appropriately set by a person skilled in the art. For example, a person skilled in the art can select an administration method needed according to the specific disease state. Specific modes of the administration method include, but are not limited to, injections (such as intravenous, subcutaneous, intramuscular, intraperitoneal, and injection to the affected part), oral, suppository, and transdermal administrations (such as application).

The present invention provides a method for treating or preventing a disease associated with viral infection, comprising the step of administering a substance capable of suppressing the expression or activity of the protein encoded by the target gene. The subject to be administered, administration method, dose, etc. are as described above.

The present invention further provides a substance capable of suppressing the expression or activity of the protein encoded by the target gene, for use in treatment or prevention of symptoms caused by viral infections.

The present invention further provides the use of a substance capable of suppressing the expression or activity of the protein encoded by the target gene for producing a pharmaceutical composition for treatment and/or prevention of symptoms caused by viral infections.

The antiviral drug of the present invention may be used in combination with other agents effective against viral infection. They may be administered separately during the course of treatment, or may be administered in combination with the antiviral drug of the present invention, for example, in a single dosage form such as a tablet, intravenous solution or capsule. The other agents effective against viral infections include viral growth inhibitors. Examples of the virus growth inhibitors include HBV growth inhibitors such as entecavir and tenofovir; and influenza virus growth inhibitors such as oseltamivir. Viral growth inhibitors preferably used in combination with the antiviral drug of the present invention are reverse transcriptase inhibitors. When the virus is a hepatitis B virus, the viral growth inhibitor used in combination with the antiviral drug of the present invention is an HBV growth inhibitor, including in particular, interferon, peginterferon, lamivudine, adefovir, entecavir, tenofovir, telbivudine, and clevudine, among which entecavir is preferred.

The present invention relates to a screening method for an antiviral drug, the method comprising selecting a substance capable of suppressing an expression or activity of a protein encoded by a target gene as an antiviral drug from test substances, wherein the target gene is one or more genes selected from the group consisting of DOCK11, DENND2A, LIPG, and HECW2 genes. The screening method of the present invention includes the following steps:
(i) determining whether or not the test substance is a substance capable of suppressing the expression or activity of the protein encoded by the target gene; and
(ii) selecting as an active ingredient of the antiviral drug a test substance determined in the step (i) as a substance capable of suppressing the expression or activity of the protein encoded by the target gene.

By the above-described step (i), whether or not the test substance to be screened is a substance capable of suppressing the expression or activity of the protein encoded by the target gene is determined. Means for determining whether or not the substance is capable of suppressing the expression or activity of the protein encoded by the target gene can be appropriately selected from any means known to those skilled in the art and developed in the future, within the range where the object is achieved, depending on the test substance to be determined and on the expression or activity of the protein encoded by the target gene whose suppression is to be determined. For example, the expression level of the target gene in a cell capable of expressing the target gene, the level of enzymatic activity of the protein encoded by the target gene, the level of activity or function of a protein itself with which the protein encoded by the target gene interacts (associating molecule), or the binding ability or binding amount (association ability or association amount) between the protein encoded by the target gene and the protein (associating molecule) interacting with the protein encoded by the target gene may be used as an indicator. The values of such an indicator may be compared between conditions in which the test substance is absent and present, and when the value of the indicator is decreased in the presence of the test substance compared to the value in the absence of the test substance, the test substance can be determined to be a substance capable of suppressing the expression or activity of the protein encoded by the target gene.

A screening method for a substance capable of suppressing the activity of a protein encoded by a target gene (e.g., enzymatic activity, binding to an interacting protein) will be described below, with an illustration where the target gene is DOCK11 gene and the interacting protein is Rho GTPase. A screening method for a substance capable of suppressing the activity of the protein encoded by the DOCK11 gene comprises the following steps (a), (b) and (c) of:
(a) bringing Rho GTPase into contact with the protein encoded by the DOCK11 gene in the presence of a test substance;
(b) measuring the binding ability between Rho GTPase and the protein encoded by the DOCK11 gene in the presence of the test substance, and comparing the measured binding ability to the binding ability between Rho GTPase and the protein encoded by the DOCK gene in the absence of the test substance;
(c) selecting a test substance that causes a decrease in the binding ability between Rho GTPase and the protein encoded by the DOCK11 gene as an active ingredient of the antiviral drug based on the comparison result in step (b) above.

The protein encoded by the DOCK11 gene and Rho GTPase in step (a) can be prepared by known methods. For example, recombinant proteins can be prepared by gene recombination techniques. As the protein encoded by the DOCK11 gene or Rho GTPase, cells expressing these proteins may be used. Such cells may be, for example, cells expressing these proteins naturally, or cells transformed with expression vectors to express these proteins. Such cells can be easily identified or prepared by those skilled in the art and, for example, primary cultured cells, cell lines derived from the primary cultured cells, commercially available cell lines, and cell lines available from Cell Bank can be used.

In step (b), first, the binding ability between Rho GTPase and the protein encoded by the DOCK11 gene is measured in the presence of a test substance. The "binding ability" to be measured is not particularly limited so long as the binding between Rho GTPase and the protein encoded by the DOCK11 gene can be evaluated, and includes binding amount, binding strength (including parameters such as affinity constant, binding rate constant, and dissociation rate constant), and binding mode (including concentration dependent binding). The binding ability can be measured, for example, by known methods such as flow cytometry using a protein labeled with a labeling substance. Methods of measuring binding utilizing surface plasmon resonance (such as Biacore) are also suitably used.

Next, the binding ability between Rho GTPase and the protein encoded by the DOCK11 gene in the presence of the test substance is compared with the binding ability between Rho GTPase and the protein encoded by the DOCK11 gene in the absence of the test substance. While the binding ability between Rho GTPase and the protein encoded by the DOCK11 gene in the absence of the test substance may be measured before or simultaneously with the measurement of the binding ability between Rho GTPase and the protein encoded by the DOCK11 gene in the presence of the test substance, the binding ability simultaneously measured is preferred from the viewpoint of accuracy and reproducibility of the experiment.

In step (c), a test substance that causes a decrease in binding ability between Rho GTPase and the protein encoded by the DOCK11 gene is selected as an active ingredient of the antiviral drug.

Cdc42, which is a Rho GTPase, is known as an associating molecule for the protein encoded by the DOCK11 gene. It is known that the protein encoded by the DOCK11 gene mediates a positive feedback activation of Cdc42. It has been reported that activated Cdc42 binds to the protein encoded by the DOCK11 gene and then enhances its guanyl nucleotide exchange factor (GEF) activity (Lin, Q., Yang, W., Baird, D., Feng, Q., Cerione, R. A., 2006. J. Biol. Chem. 281, 35253-35262). Therefore, as a means for determining a substance capable of suppressing the expression or activity of the protein encoded by the DOCK11 gene, the binding ability between the said protein and Cdc42 can be measured, as described in the explanation of step (b) above. Or, for example, measurements of the activity of Cdc42 itself and the GEF activity enhanced by Cdc42 are exemplified as such means. The GEF activity can be measured using a GEF assay system described below.

When the target gene is DENNDA2A gene, Rabs, in particular Rab9, is known as proteins which interact therewith (associating molecules). Means for determining a substance capable of suppressing the expression or activity of the protein encoded by the DENND2A gene include measuring the binding ability between the said protein and Rab9, or measuring the GEF activity or the activity of Rab9 itself. The GEF activity can be measured using a GEF assay system (J. Cell. Biol. Vol. 191, 367-381, 2010) as described below or known assay kits. It is known that the protein encoded by the DENND2A gene has a function of releasing GDP particularly from Rab9a or Rab9b.

The GEF assay system will be described in detail with an illustration in the case of Rab.

Ten micrograms of GST-tagged Rab are incubated in 200 µl of loading solution (50 mM Hepes-NaOH (pH 6.8), 0.1 mg/ml BSA, 125 µM EDTA, 10 µM Mg-GDP, and 5 µCi[3H]-GDP (10 mCi/ml; 5,000 Ci/mmol) for 15 minutes at 30° C. to obtain a reaction solution containing Rab to which Gab is added.

As a standard GEF reaction, 100 µl of the above-described reaction solution is mixed with 10 µl of 10 mM Mg-GTP and 10-100 nM GEF (i.e., the protein encoded by the DENND2A gene) or a control buffer, and an assay buffer is added to the resulting mixture to bring the final volume to 120 µl. GEF reaction is carried out for 20 minutes at 30° C. to replace GDP with GTP.

Thereafter, 2.5 µl of the resultant solution is separated for activity measurement. The remaining solution is divided into two tubes and incubated with 500 µl of ice cold assay buffer containing 1 mM MgCl$_2$ and 20 µl of packed glutathione-sepharose for 60 minutes at 4° C. The sepharose is transferred to a vial containing 4 ml of scintillation solution, and the amount of released GDP (pmol) is measured, which can be the GEF activity (the amount of nucleotide exchange).

Instead of the amount of released GDP, the amount of bound GTP may be measured. The amount of bound GTP can be measured by using only unlabeled GDP without using labeled GDP in the above-described loading solution, and using 0.5 µl of 10 mM GTP and 1 µCi[35S]-GTP•S32 (10 mCi/ml; 5,000 Ci/mmol) instead of Mg-GTP in the GEF reaction.

When the target gene encodes an enzyme, the screening method for a substance capable of suppressing the activity of a protein encoded by a target gene can be carried out by: bringing a substrate into contact with the enzyme in the presence of a test substance and allowing them to react in the above-described step (a); measuring the enzyme activity instead of the binding ability in the above-described step (b); and selecting a test substance that causes a decrease in the enzyme activity in the above-described step (c). When the target gene is the LIPG gene, the enzyme activity can be determined by measuring the lipase activity as shown below (see, Nature genetics, 21,424 (1999)) in which measurement for the reactant is carried out. When the target gene is the HECW2 gene, the enzyme activity can be determined by measuring the ubiquitin transferase activity as shown below (see Biochemical and Biophysical Research Communications 308 (2003) 106-113).

The method for measuring the lipase activity is illustrated in detail below.

The activity of the protein encoded by the LIPG gene can be determined by an assay for triglyceride (TG) lipase. In glycerol, 9,10-3H(N)-triolein (250 µCi; NEN) is mixed with unlabeled triolein (150 mg) and type IV-S-a lecithin (9 mg; Sigma). The mixture is concentrated and emulsified, and the emulsified substrate is mixed with Tris-HCl (0.2 M, pH 8.0) containing 3% (w/v) fatty acid free BSA and heat inactivated bovine serum to prepare a reaction substrate. The reaction substrate and LIPG-expressing cells are brought into contact with each other in a medium and incubated at 37° C. for 2 hours to allow the reaction to occur. The reaction can be stopped by adding methanol-chloroform-heptane (1.41: 1.25:1) thereto and mixing potassium carbonate-borate buffer therewith. The reactant is centrifuged, and the supernatant is used for measurement with a scintillation counter to measure TG lipase activity.

An assay for phospholipase can be carried out as follows. First, an emulsion of phosphatidylcholine (PC) is mixed with 14C-dipalmitoyl PC (2 µCi; NEN), lecithin (10 µl), Tris-TCNB (100 µl; 100 mM Tris-HCl, pH 7.4, 1% Triton X-100, 5 mM CaCl$_2$), 200 mM NaCl, 0.1% BSA), and then the mixture is stirred and dried with an evaporator. The dried lipid is mixed in TCBN to prepare a reaction substrate. The reaction substrate is mixed with a PC emulsion, MEM medium, etc., and then LIPG-expressing cells and the substrate are brought into contact with each other and incubated at 37° C. for about 2 hours to allow the reaction to occur. The reaction is stopped by adding HCl. Next, the resulting mixture is extracted with 2-propanol:hexane (1:1), and then the upper hexane layer is filtered through a silica gel column. The 14C free fatty acid contained in the filtrate is measured with a scintillation counter to measure the phospholipase activity.

The method for measuring the activity of ubiquitin transferase in connection with HECW2 gene is illustrated in detail below.

A protein encoded by the HECW2 gene is mixed with an appropriate solution containing E1 (ubiquitin-activating enzyme) and E2 (ubiquitin-conjugating enzyme) and bovine ubiquitin (Sigma, Chemical), and incubated at 30° C. for 2 hours to allow the reaction to occur. The reaction is stopped by adding SDS solution (containing 62.5 mM Tris-Cl, pH 6.8, 2% SDS, 10% glycerol, 0.1 M DTT, 0.01% bromophenol blue) and boiling. Next, the solution is subjected to electrophoresis on SDS polyacrylamide gel followed by immunoblotting to detect ubiquitinated proteins, thereby allowing measurement of the ubiquitin transferase activity.

The present invention includes a screening method for an antiviral drug capable of suppressing the expression of a target gene or the activity of a protein encoded by the target gene, the method comprising the following steps (a) to (c) of:

(a) bringing a cell into contact with a test substance in a system in which the cell expresses the target gene;

(b) measuring the expression level of the target gene in the cell and comparing the expression level of the target gene in the cell contacted with the test substance to the expression level of the target gene in the cell not contacted with the test substance; and (c) selecting a test substance that causes a decrease in the expression level of the target gene in the cell as an antiviral drug through screening based on the comparison result in step (b) above.

The system in which a cell expresses the target gene may be any system as long as the cell capable of expressing the target gene is in the presence of a factor that enhances the expression of the target gene, and no particular limitation is imposed on whether the factor is present intracellularly or extracellularly. For example, the system may be a cell line into which a promoter for constitutively expressing the target gene is incorporated.

A screening method for a substance capable of suppressing the expression of the target gene comprises the following steps (a'), (b') and (c') of:

(a') bringing a test substance into contact with cells in which the expression of the target gene or the protein encoded by the target gene can be measured;
(b') measuring the expression level in the cells contacted with the test substance and comparing the expression level to the expression level in control cells not contacted with the test substance;
(c') selecting a test substance that causes a decrease in the expression level as an active ingredient of the antiviral drug based on the comparison result of step (b') above.

In the above step (a'), the test substance is placed in contact with cells in which the expression of the target gene or the protein encoded by the target gene can be measured. The test substance may be brought into contact with the cells in which the expression of the target gene or the protein encoded by the target gene can be measured in a culture medium.

"Cells in which the expression of the target gene or the protein encoded by the target gene can be measured" refers to cells in which the expression level of the product from the target gene, such as transcription product or translation product (i.e., protein) can be evaluated. The cells in which the expression level of the product from the target gene can be evaluated may be cells that can naturally express the target gene or cells that allow reporter assay for the transcriptional regulatory domain of the target gene. These cells can be easily identified by those skilled in the art and, for example, primary cultured cells, cell lines derived from the primary cultured cells, commercially available cell lines, and cell lines available from Cell Bank can be used.

In the above-described step (b'), the expression level of the target gene or the protein encoded by the target gene in cells contacted with the test substance is first measured. The expression level may be measured using methods known per se, the method being selected in consideration of, for example, the type of the cells used. For example, transcription products may be measured by preparation of total RNA from cells and subsequent RT-PCR, Northern blotting or the like, and translation products may be measured by preparation of extracts from cells and subsequent immunological procedures. When cells that allow reporter assay for the transcriptional regulatory domain of the target gene are used, the expression level may be measured based on the signal intensity of the reporter.

Next, the expression level of the target gene or the protein encoded by the target gene in the cells contacted with the test substance is compared with the expression level of the target gene or the protein encoded by the target gene in control cells not contacted with the test substance. The comparison of the expression levels is carried out based on whether a significant difference is found or not. While the expression level of the target gene or the protein encoded by the target gene in control cells not contacted with the test substance may be measured before or simultaneously with the measurement of the expression level of the target gene or the protein encoded by the target gene in the cells contacted with the test substance, the expression level simultaneously measured is preferred from the viewpoint of accuracy and reproducibility of the experiment.

In the step (c'), a test substance that causes a decrease in the expression level of the target gene or the protein encoded by the target gene is selected as an active ingredient of the antiviral drug.

The above-mentioned test substance is not particularly limited as long as it can be a candidate substance for an active ingredient of the antiviral drug. The above-mentioned test substance may be a natural compound (e.g., a substance derived from an organism) or a synthetic compound. Preferably, the above-mentioned test substance is a substance which is pharmaceutically acceptable for use in human. Specific examples of the test substance include, but are not limited to, low molecular weight compounds; proteins such as antibodies; nucleic acids capable of suppressing the expression of proteins (e.g., siRNA, shRNA, dsRNA, miRNA); and sugar chains or complex carbohydrates.

The present invention also includes a method of detecting a gene having an action of retaining virus-derived nucleic acid in the host cell from host cell-derived genes, the method comprising analyzing a host cell after viral infection for the expression patterns of two or more finite numbers of genes. Comprehensive single-cell gene expression analysis (International Publication WO2015/166768) for human hepatocellular carcinoma cell lines established from a hepatitis B-positive patient with hepatocellular carcinoma makes it possible to carry out comparison of the gene expression pattern between HBV-positive and HBV-negative hepatocellular carcinoma cells established from the same cancer patient, as shown in the present invention. In embodiments of the present invention, HBV-positive hepatocellular carcinoma cells and HBV-negative hepatocellular carcinoma cells have the same genome. By comparing the gene expression patterns in both cells, genes acting on the HBV retention mechanism can be effectively detected. The expression of HBV gene is rarely retained in human hepatocellular carcinoma cell lines established from hepatocellular carcinoma tissues from a specific cancer patient. According to the present invention, utilizing such a rare phenomenon, a gene having an action of retaining virus-derived nucleic acid in a host cell can be detected. The virus-derived nucleic acid in a host cell may be DNA or RNA. The DNA includes cccDNA of HBV.

The method of detecting a gene having an action of retaining virus-derived nucleic acid in a host cell of the present invention comprises the following steps of:
(1) establishing a virus-positive cell line from virus-positive tissue specimen collected from a single organism;
(2) subculturing the virus-positive cell line to prepare a virus-positive cell and a virus-negative cell;
(3) analyzing the virus-positive cell and virus-negative cell obtained in the step (2) for the expression patterns of two or more finite numbers of genes in each single cell;
(4) comparing the expression pattern of the genes in the virus-positive cell with the expression pattern of the genes in the virus-negative cell; and
(5) selecting a gene having a higher expression level in the virus-positive cell as compared with the virus-negative cell, as the gene having an action of retaining virus-derived nucleic acid in the host cell.

Factors having an action of retaining virus-derived nucleic acid in a host cell can be detected efficiently by comparing virus-positive cell(s) and virus-negative cell(s) that have occurred under the same conditions. In the method for detecting the gene of the present invention, in order to compare virus-positive cell(s) and virus-negative cell(s) that have occurred under the same conditions, virus-positive cell(s) and virus-negative cell(s) both derived from a single organism are used. The single organism means a single individual, and does not mean obtaining virus-positive cell(s) and virus-negative cell(s) from two or more individuals. More specifically, a virus-positive tissue specimen is collected from a single organism. The term "virus-positive" means being infected with each virus, and means that a marker(s) for the virus (e.g., virus-derived antigens, antibodies against the antigens, virus-derived nucleic acids (e.g., DNA, mRNA)) is/are detected. The term "virus-negative" means that a marker(s) of the virus and the like is/are not detected. For example, the term "HBV-positive" means that at least one of cccDNA and HBV DNA is found at a detectable level and HBV mRNA is expressed. In embodiments of the present invention, a tissue specimen refers to those obtained by collecting part or all of virus-positive organs and tissues from various virus-positive organs and tissues of an organism. A virus-positive cell line can be obtained by treating a tissue specimen with an agent or the like, separating it into single cells to form a suspension. A virus-positive cell line may be produced by such a method, or a virus-positive cell line already established from a virus-positive tissue specimen may be obtained and used. Subculturing of a virus-positive cell line results in a decrease in the proportion of virus-positive cells. The passage number in subculturing is not particularly limited as long as the object of the present invention is not impaired, and it is required that while virus-positive cells are decreased, virus-positive cells are still not completely disappeared. For example, a passage number in the range of about 10 to 40 is preferred. By such subculturing, two types of cells, virus-positive cell(s) and virus-negative cell(s), derived from a single organism are generated.

Expression patterns of two or more finite numbers of genes in each single cell may be analyzed by any method, for example, a comprehensive single-cell gene expression analysis disclosed in International Publication WO2015/166768. Specifically, this is a method of analyzing the constitution of nucleic acids derived from a single cell using a microplate having a plurality of reaction wells. On the microplate, one bead is placed in one reaction well. A plurality of single-stranded oligonucleotide molecules are bound to one bead, and in the single-stranded oligonucleotide, a nucleic acid-capturing sequence is exposed at the 3' end, and a barcode sequence is contained 5' upstream to the nucleic acid-capturing sequence. Each bead has a specific barcode sequence different from the other barcode sequences the other beads have. The comprehensive single-cell gene expression analysis comprises the following steps (i) to (iii) of:
(i) seeding cells in a microplate to place one cell in one reaction well, extracting nucleic acids from the cells in the reaction wells of the microplate, and allowing the nucleic acids derived from each cell to be captured by single-stranded oligonucleotides on each bead;
(ii) performing a nucleic acid amplification reaction using the nucleic acids captured by the single-stranded oligonucleotides on the beads as templates to obtain amplified fragments; and
(iii) checking barcode sequences in the obtained amplified fragments and identifying fragments having the same barcode sequences as fragments derived from the same cell.

In the method of detecting a gene having an action of retaining virus-derived nucleic acid in a host cell of the present invention, it is preferred that the virus express transcription products comprising poly A at their 3' ends from genes derived from the virus. Thanks to production of transcription products (mRNAs) comprising poly A at their 3' ends in the cell by the virus, host-derived mRNAs and virus-derived mRNAs can be simultaneously captured and analyzed in the step (i) of the comprehensive single-cell gene expression analysis described above. Through analysis of the expression patterns of the genes in the step (3) in the detection method of the present invention, cells expressing a virus-derived gene are identified as virus-positive cells and cells not expressing a virus-derived gene are identified as virus-negative cells. Such a virus is preferably a hepatitis B virus, and the gene having an action of retaining virus-derived nucleic acid in a host cell is preferably a gene having an action of retaining cccDNA derived from hepatitis B virus in a host cell.

EXAMPLES

The present invention will be described in detail with reference to Reference Examples and Examples below, but is not limited to the following Reference Examples and Examples. The following Reference Examples and Examples were conducted with the approval of the ethics committee of Kanazawa University.

(Reference Example 1) Preparation of Polydimethylsiloxane (PDMS) Slide for Comprehensive Single-Cell Gene Expression Analysis According to the method described in the International Publication WO2015/166768, a PDMS slide for comprehensive single-cell gene expression analysis was prepared. First, emulsion PCR was carried out using a barcode linker to prepare beads to which PCR amplification products were bound, and then the beads were purified. The obtained beads were treated with restriction enzymes, alkali and heat shock, to prepare beads to the surface of which several millions of oligonucleotide molecules consisting of single-stranded DNAs were bound. Different barcode sequences were given to the individual beads, respectively. The sequence of the barcode linkers is as follows, which is shown in SEQ ID NO: 20.

```
Barcode linkers (SEQ ID NO: 20):
5'-CCATCTCATCCCTGCGTGTCTCCGACTCAGGCAGTGAAAAAAAAAAA
AAAAAAAAAAAAAANNNNNNNNNNNNACATAGGCCGTCTTCAGCCGCTG
AGACTGCCAAGGCACACAGGGGATAGG-3'
N = A or T or C or G
```

The prepared beads were placed one by one in wells of a PDMS slide to prepare a PDMS slide for comprehensive single-cell gene expression analysis.

(Example 1) Screening of Target Genes for Anti-HBV Drugs (1) HBV-Positive Human Hepatoma Cell Lines Used A KM cell line, which is a human hepatocellular carcinoma (HCC) cell line established from a specific hepatitis B-positive patient with hepatocellular carcinoma, was obtained from the First Department of Internal Medicine, Kanazawa University Hospital. The KM cell line was established by obtaining a human HCC specimen from a hepatitis B-positive patient with hepatocellular carcinoma who underwent radical operation at the Liver Center, Kanazawa University Hospital after acquiring informed consent, collecting an HCC tissue from the specimen, and separating the tissue into single cells in a suspension immediately after the collection.

Detection of HBV cccDNA, HBV DNA, and HBV mRNA (i.e., pgRNA) in KM cells after the establishment and KM cells subcultured after the establishment was carried out. In addition, immunostaining for HBc antigen, which was known as a marker for HBV, was carried out to observe the HBc-positive cells. Specifically, the detection was carried out as follows.

(i) Quantitative RTD-PCR

Total RNAs were isolated using GenElute™ Mammalian Total RNA Miniprep Kit (Sigma-Aldrich Japan K.K., Tokyo, Japan), and cDNAs were synthesized using High Capacity cDNA reverse transcription kit (Applied Biosystems, Carlsbad, Calif.).

RTD-PCR was carried out using 7500 Real Time PCR System (Applied Biosystems, Carlsbad, Calif.) according to the manufacturer's instruction. The primers and probes used are as follows.

```
Primers for pg RNA:
                                    (SEQ ID NO: 21)
5'GCTCTGTATCGGGAGGCCTTA3',
and (SEQ ID NO: 22)
5'TGAGTGCTGTATGGTGAGGAGAA3'

Probe for pg RNA:
                                    (SEQ ID NO: 23)
5'FAM-AGTCTCCGGAACATT-MGB3'

Primers for PreS/S:
                                    (SEQ ID NO: 24)
5'ACCCCAACAAGGATCATTGG3',
and (SEQ ID NO: 25)
5'CGAATGCTCCCGCTCCTA3'

Probe for PreS/S:
                                    (SEQ ID NO: 26)
5'FAM-CAGAGGCAAATCAG-MGB3'

Primers for HBx:
                                    (SEQ ID NO: 27)
5' TGTCAACGACCGACCTTGAG3',
and (SEQ ID NO: 28)
5' CCCAACTCCTCCCAGTCCTT3'

Probe for HBx:
                                    (SEQ ID NO: 29)
5'FAM-CATACTTCAAAGACTGTTTGTT-MGB3'
```

(ii) Determination of the Amounts of HBV DNA and HBV cccDNA by Quantitative PCR

The amount of intracellular HBV DNA was determined using DNeasy Blood & Tissue Kit (QIAGEN) according to the protocol of the product. The amount of HBV DNA in the medium was determined using SMI TEST EX R&D Kit (MLB) according to the protocol of the product. The amount of HBV DNA was determined by quantitative PCR using 5'ACTCACCAACCTCCTGTCCT3' (SEQ ID NO: 30) and 5"GACAAACGGGCAACATACCT3' (SEQ ID NO: 31) as a primer set, and 5'FAM-TATCGCTGGATGTGTCTGCG-GCGT-TAMRA3' (SEQ ID NO: 32) as a probe.

The extracted DNA (50 ng) was treated with 10 U Plasmid safe DNase1 (Epicenter) at 37° C. for 60 minutes and then treated at 70° C. for 30 minutes to inactivate the DNase. The amount of cccDNA was determined by quantitative PCR using 5'CGTCTGTGCCTTCTCATCTGC3' (SEQ ID NO: 33) and 5'GCACAGCTTGGAGGCTTGAA3' (SEQ ID NO: 34) as a primer set, and 5'FAM-CTGTAGG41CATAAATTGGT-MGB3' (SEQ ID NO: 35) as a probe.

(iii) Indirect Immunofluorescence Staining

Indirect immunofluorescence staining was carried out using rabbit anti-HBcAg polyclonal antibody (an antibody against HBc antigen: Thermo Fisher Scientific Inc.). Cultured cells were fixed with methanol-acetone (1:1) for 10 minutes and then permeabilized with 0.01% Triton X-100 (Merck) in 10 mmol/L phosphate buffered saline at room temperature for 10 minutes. The cells were incubated in phosphate buffered saline containing 5% BSA for 30 minutes and then incubated with rabbit anti-HBcAg polyclonal antibody diluted in phosphate buffered saline containing 3% BSA overnight at 4° C. The cells were washed with phosphate buffered saline containing Tween 20 and then incubated with secondary antibody Alexa 488-conjugated donkey anti-goat antibody and Alexa 594-conjugated donkey anti-rabbit antibody (Life Technologies) for 1 hour at room temperature. Nuclei were stained with DAPI (Dojindo Laboratories, Co., Ltd.). The numbers of liver cells and HBV-positive liver cells were counted to analyze the ratio of HBV-positive liver cells.

Figure 13:
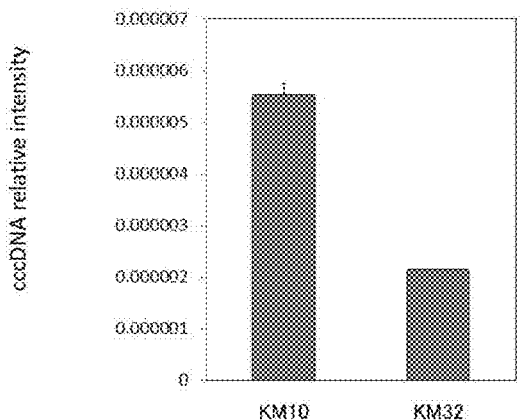
FIG. 13 shows the results of measuring the amount of HBV cccDNA in HBV-positive hepatoma cells (KM cells) when passaged 10 times and when passaged 32 times. (Example 1)

As a result, in early KM cells after the establishment, HBV cccDNA and HBV DNA were both observed at detectable levels, and expression of HBV mRNA was also observed. However, the amounts of HBV cccDNA and HBV mRNA in KM cells were decreased with subculturing. For example, it was confirmed that the amount of HBV cccDNA in KM cells passaged 32 times was decreased to less than half the amount in KM cells passaged 10 times (FIG. 13). In addition, when HBc antigen known as an HBV marker was immunostained, HBc positive cells were less than 0.1% in total cells.

(2) Comprehensive Single-Cell Gene Expression Analysis Using HBV mRNA

Comprehensive single-cell gene expression analysis of a human HCC cell line established from a hepatitis B-positive patient with hepatocellular carcinoma was carried out using the PDMS slide for comprehensive single-cell gene expression analysis prepared in Reference Example 1.

First, cells were placed on the above-mentioned PDMS slide for comprehensive single-cell gene expression analysis. After leaving it to stand for 10 to 15 minutes, the slide was washed with PBS and covered with a dialysis membrane (12,000 to 14,000 MWCO regenerated cellulose dialysis tube, 25-mm flat width, Fisher Scientific). Then, Lysis buffer (500 mM LiCl in 100 mM TRIS buffer (pH 7.5) with 1% lithium dodecyl sulfate, 10 mM EDTA and 5 mM DTT) was added from the upper side of the dialysis membrane to extract mRNAs in the cells, and then allowed the mRNAs to be captured by oligonucleotides on beads. After the beads were collected, mRNAs bound to the beads were subjected to reverse transcription reaction to synthesize the 1st strand cDNA. Next, the 2nd strand was synthesized by PCR to obtain amplification products. The amplified products were sequenced using a next generation sequencer HiSeq 2500 (Illumina Inc.).

About 900 million reads were sequenced by the next generation sequencer, and the expression levels of human mRNA and HBV mRNA were analyzed using the barcode sequences. As a result, it was revealed that only one cell expressed HBV mRNA in 3,000 cells. Among the genes specifically expressed in HBV mRNA-positive cells, LIPG gene, DENND2A gene, DOCK11 gene, and HECW2 gene were confirmed as genes showing high expression (Table 1).

TABLE 1

| Gene | Number of positive cells in 500 cells | Expression level in an HBV positive cell (/million reads) | Official Full Name | Refseq | Gene Ontology Function |
|---|---|---|---|---|---|
| LIPG | 10 | 210 | lipase, endothelial | NM_006033 | lipoprotein lipase activity, phosphatidylcholine 1-acylhydrolase activity, phospholipase activity |
| DENND2A | 3 | 203 | DENN/MADD domain containing 2A | NM_015689 | Rab guanyl-nucleotide exchange factor activity |
| DOCK11 | 2 | 96 | dedicator of cytokinesis 11 | NM_144658 | Rho GTPase binding, Rho guanyl-nucleotide exchange factor activity, protein binding |
| HECW2 | 1 | 13 | HECT, C2 and WW domain containing E3 ubiquitin protein ligase 2 | NM_020760 | ligase activity, ubiquitin-protein transferase activity |

(Example 2) Determination of shRNA Function Against Each Target Gene

Five shRNAs were prepared for DOCK11 gene that was specifically expressed in HBV-positive human hepatoma cells, and the effect of suppressing the expression of DOCK11 gene by each shRNA was determined.

HepG2.2.15 cells were infected with lentivirus expressing each shRNA against the DOCK11 gene (Sigma-Aldrich Japan K.K., Tokyo, Japan, TRCN0000369589, TRCN0000369590, TRCN0000369611, 1RCN0000376430, TRCN0000123016; sequences #1 to #5 of five shRNAs are shown below) according to a conventional method, and 72 hours later, the amount of mRNA of DOCK11 gene, the amount of HBV DNA, and the amount of HBV cccDNA were determined. The amounts of HBV DNA and HBV cccDNA were measured in the same manner as in Example 1. The mRNA of DOCK11 gene was quantified by real time PCR according to a conventional method.

```
DOCK11 #1:
                                      (SEQ ID NO: 1)
CCGGCCAACAGGGTGCTTACATATTCTCGAGAATAT
GTAAGCACCCTGTTGGTTTTTG

DOCK11 #2:
                                      (SEQ ID NO: 2)
CCGGGTACTAGACACCATATCATTTCTCGAGAAATG
ATATGGTGTCTAGTACTTTTTG

DOCK11 #3:
                                      (SEQ ID NO: 3)
CCGGACTAAATGAGCGGCTAATTAACTCGAGTTAAT
TAGCCGCTCATTTAGTTTTTG

DOCK11 #4:
                                      (SEQ ID NO: 4)
CCGGTGATGGCCATAACCCATTAATCTCGAGATTAAT
GGGTTATGGCCATCATTTTTG

DOCK11 #5:
                                      (SEQ ID NO: 5)
CCGGCCAGGCTACTTGAATCTGAATCTCGAGATTCAG
ATTCAAGTAGCCTGGTTTTTG
```

HepG2.2.15 cells are cells which have been established by transfecting HepG2 human hepatoma-derived cells with HBV and continuously produce the virus (Proc. Natl. Acad. Sci. USA., 84: 1005-1009 (1987), Journal of Virology, August 1988, 62, 2836-2844). HepG2.2.15 cells were maintained in DMEM medium (Life Technologies, Carlsbad, Calif.) containing 10% fetal bovine serum (FBS), 100 U/mL penicillin and 100 μg/mL streptomycin until use.

Similarly, the functions of DENND2A, LIPG, and HECW2 genes were also confirmed using lentiviruses (Sigma-Aldrich Japan K.K., Tokyo, Japan, TRCN0000179931, TRCN0000178923, TRCN0000184030, TRCN0000179932, TRCN0000372782, TRCN0000378899, TRCN0000050893, TRCN000005044894, TRCN0000372783, TRCN0000004789, TRCN0000004790, TRCN0000004791, TRCN0000004792, TRCN0000004793) respectively expressing shRNAs shown in SEQ ID NOs: 6 to 19.

```
DENND2A #1:
                                      (SEQ ID NO: 6)
CCGGCTGAAGGGACTAGGCAATAAACTCGAGTTTA
TTGCCTAGTCCCTTCAGTTTTTG

DENND2A #2:
                                      (SEQ ID NO: 7)
CCGGCCAATGAAGGAGAACCCTTATCTCGAGATAA
GGGTTCTCCTTCATTGGTTTTTG

DENND2A #3:
                                      (SEQ ID NO: 8)
CCGGCCTAGTGCAGCCCTATTCTTTCTCGAGAAAG
AATAGGGCTGCACTAGGTTTTTG

DENND2A #4:
                                      (SEQ ID NO: 9)
CCGGCTAGTGCAGCCCTATTCTTTACTCGAGTAAA
GAATAGGGCTGCACTAGTTTTTG

LIPG #1:
                                      (SEQ ID NO: 10)
CCGGACGATGTCTTGGGATCAATTGCTCGAGCAATTGATC
CCAAGACATCGTTTTTG

LIPG #2:
                                      (SEQ ID NO: 11)
CCGGATGCAGGCAACTTCGTGAAAGCTCGAGCTTTCACG
AAGTTGCCTGCATTTTTTG

LIPG #3:
                                      (SEQ ID NO: 12)
CCGGCCGTTGTAATAGCATTGGCTACTCGAGTAGCCAAT
GCTATTACAACGGTTTTTG

LIPG #4:
                                      (SEQ ID NO: 13)
CCGGCGTCACCCTTTATGGCACTAACTCGAGTTAGTGCC
ATAAAGGGTGACGTTTTTG

LIPG #5:
                                      (SEQ ID NO: 14)
CCGGTTACACGGATGCGGTCAATAACTCGAGTTATTGAC
CGCATCCGTGTAATTTTTG
```

-continued

HECW2 #1:
(SEQ ID NO: 15)
CCGGGCCCAAACATTTCTTTGAGATCTCGAGATCTCA
AAGAAATGTTTGGGCTTTTT

HECW2 #2:
(SEQ ID NO: 16)
CCGGCCAGGGAAGTTAAAGTTAATTCTCGAGAATTAA
CTTTAACTTCCCTGGTTTTT

HECW2 #3:
(SEQ ID NO: 17)
CCGGGCACAATACTTGGAGTCAATTCTCGAGAATTGA
CTCCAAGTATTGTGCTTTTT

HECW2 #4:
(SEQ ID NO: 18)
CCGGGCTTACAATGACAAGATTGTTCTCGAGAACAAT
CTTGTCATTGTAAGCTTTTT

HECW2 #5:
(SEQ ID NO: 19)
CCGGCCCTTATCTTAAGATGTCAATCTCGAGATTGAC
ATCTTAAGATAAGGGTTTTT

The results are shown in FIGS. 1 to 4. It was confirmed that the amounts of HBV DNA and cccDNA could be decreased by using shRNAs against DOCK11, DENND2A, LIPG and HECW2 genes.

(Example 3) Determination of shRNA Function Against HBV Infection

Using fresh human hepatocytes (PHH cells) derived from PXB mouse (PhoenixBio Co., Ltd., Hiroshima, Japan), effects of shRNAs against each gene on infection of human hepatocytes with HBV were determined. Experiments were carried out by culturing PHH cells as follows. First, on day 0 of culture, the cells were infected with the lentivirus expressing the shRNA against each of the genes by a conventional method. A serum collected from an HBV-infected chimeric mouse infected with HBV (Genotype C. 5 HBV DNA copies/cell) was added to the cells as an HBV inoculum on day 1 of culture. On day 2 of culture, the cells were washed three times and entecavir (ETV) (10 nM) was added thereto. On day 7 of culture, the cells were collected and the amount of HBV DNA, the amount of HBV cccDNA, and the mRNA level of each gene were determined. The amounts of HBV DNA, HBV cccDNA, and pg RNA were quantified in the same manner as in Example 1. The mRNA level of each gene was quantified in the same manner as in Example 2. shRNAs having the base sequences shown in SEQ ID NOs: 2, 7, 14, and 17, respectively (Sigma-Aldrich Japan K.K., Tokyo, Japan, lentiviruses expressing TRCN0000369590, TRCN0000178923, TRCN0000372783, TRCN0000004791) were used against the respective genes. dHCGM medium (Yamasaki C, et al., J Hepatol. 2006, 44: 749-57) was used for the culture of fresh human hepatocytes (PHH cells).

The results are shown in FIGS. 5 to 8. The amount of cccDNA was dramatically decreased by the shRNA against DOCK11 gene or DENND2A gene, and decreased to below the detection sensitivity by combined use of ETV. The amount of cccDNA was decreased by the shRNA against LIPG gene or HECW2 gene, and a synergistic effect to decrease cccDNA was observed by combined use of ETV.

(Example 4) Determination of shRNA Function Against HBV Infection 2

In the same manner as in Example 3 and using PHH cells, effects of shRNAs against individual genes on infection of human hepatocytes with HBV were determined when the cells were cultured for a long period. Experiments were carried out by culturing PHH cells as follows. First, on day 0 of culture, the cells were infected with the lentivirus expressing the shRNA against each of the genes by a conventional method. A serum collected from an HBV-infected chimeric mouse infected with HBV (Genotype C, 5 HBV DNA copies/cell) was added to the cells as an HBV inoculum on day 1 of culture. Thereafter, the cells were cultured according to the following (1) to (4).

(1) PHH cells infected with HBV were cultured for 4 weeks.
(2) PHH cells infected with HBV were cultured for 2 weeks, then washed three times, treated with ETV (10 nM), and cultured for 2 weeks.
(3) PHH cells were infected with HBV, then at the day 2 of culture the cells were washed three times, treated with ETV (10 nM), and cultured for 2 weeks. Thereafter, the cells were washed three times to remove ETV and cultured for 2 weeks.
(4) PHH cells were infected with HBV, then at the day 2 of culture the cells were washed three times, treated with ETV (10 nM), and cultured for 4 weeks.

After carrying out the cultures (1) to (4) above, the cells were collected, and the mRNA level of each gene, the amount of HBV cccDNA, and the amount of pg RNA were determined in the same manner as in Examples 1 and 2. shRNAs having the base sequences shown in SEQ ID NOs: 2, 7, 14, and 17, respectively (Sigma-Aldrich Japan K.K., Tokyo, Japan, lentiviruses expressing TRCN0000369590, TRCN0000178923, TRCN0000372783, TRCN0000004791) were used against the respective genes.

The results are shown in FIGS. 9 to 12. In FIGS. 9 to 12, the last number in each item on the horizontal axis indicates the culture conditions (1) to (4) above. For example, "sh DOCK11 1" indicates that shRNA against DOCK11 gene was introduced and the cells were cultured under the condition (1) above. "Cont" is a result obtained when the cells were cultured without introduction of shRNA of each gene.

It was found that all the 4 genes decreased the amount of cccDNA to below the detection limit without combined use by carrying out long-term culture for 3 weeks or longer.

(Example 5) Determination of Action of Target Gene by Genome Editing

In HepG2.2.15 cells, which had been established by transfecting HepG2 human hepatoma cells with HBV, the DENND2A and Dock11 genes were knocked down using CRISPR/Cas 9 system. The amounts of HBV DNA, HBV cccDNA, and pg RNA in the HepG2.2.15 cells in which the target genes were knocked down were determined in the same manner as in Example 1.

Figure 14:
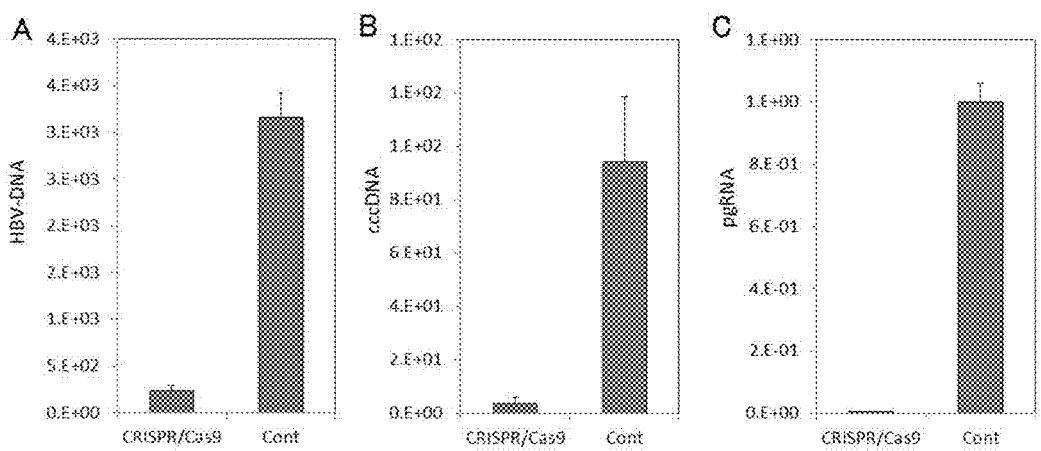
FIG. 14 shows the effects of the DOCK11 gene knockdown by genome editing on: the amount of HBV DNA (A); the amount of HBV cccDNA (B); and the expression level of pg RNA (C), which were investigated using an HBV infection system in human hepatocytes. In the panel (C), the expression levels are expressed as relative values by taking the control level as 1. (Example 5)

The results are shown in FIG. 14. It was confirmed that knockdown of Dock11 gene decreased the amount of HBV cccDNA in HepG2.2.15 cells to about 5% of the control compared. It was thus demonstrated that the Dock11 gene plays an important role in retaining cccDNA of HBV in host cells.

(Example 6) Determination of shRNA Function Against HBV Infection 3

The effects of an shRNA on the proliferation of HBV when PHHs were infected with HBV and then treated with an shRNA were investigated. One week after PHHs were infected with HBV, the shRNA (SEQ ID NO: 2) against Dock11 gene was introduced and the cells were cultured for 3 weeks with culture medium changes. Thereafter, the mRNA expression level of DOCK11 gene, the amount of HBV cccDNA, and the amount of pg RNA in the PHHs were determined in the same manner as in Examples 1 and 2.

Figure 15:
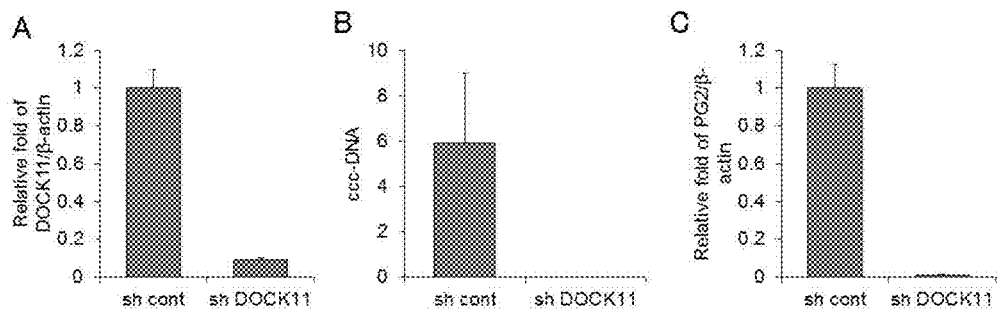
FIG. 15 shows the effects of introduction of an shRNA against DOCK11 gene on: the expression level of DOCK11 gene (A); the amount of HBV cccDNA (B); and the expression level of pg RNA (C), which were investigated using an HBV infection system in human hepatocytes, in which the shRNA was introduced after the HBV infection and the hepatocytes were long-term cultured after the shRNA introduction. In the panels (A) and (C), the expression levels are expressed as relative values by taking the control level (sh cont) in each panel as 1. (Example 6)

The results are shown in FIG. 15. It was found that the shRNA against Dock11 gene caused cccDNA and pgRNA of HBV to disappear even in cells in which HBV infection had been established. These results suggested that Dock11 gene contributes to retention of HBV in the host cells.

(Example 7) Intracellular Localization of Target Gene

Intracellular localizations of the proteins expressed by the respective target genes in KM cells were investigated by indirect immunofluorescence staining in the same manner as in Example 1. In addition to rabbit anti-HbcAg polyclonal antibody, an anti-HBc monoclonal antibody (Institute of Immunology; 2AHC21), an anti-LIPG antibody produced in rabbit (Sigma-Aldrich; HPA016966-100UL), an anti-NEDL2 (HECW2) antibody-N-terminal (Abeam; ab154888), an anti-NEDL2 antibody-N-terminal (Abeam; ab154888), and an anti-DOCK11 antibody (D-17) (SANTA CRUZ; sc-74610) were used as antibodies against HBV-core, LIPG, HECW2, DENND2A, and DOCK11, respectively.

Figure 16:
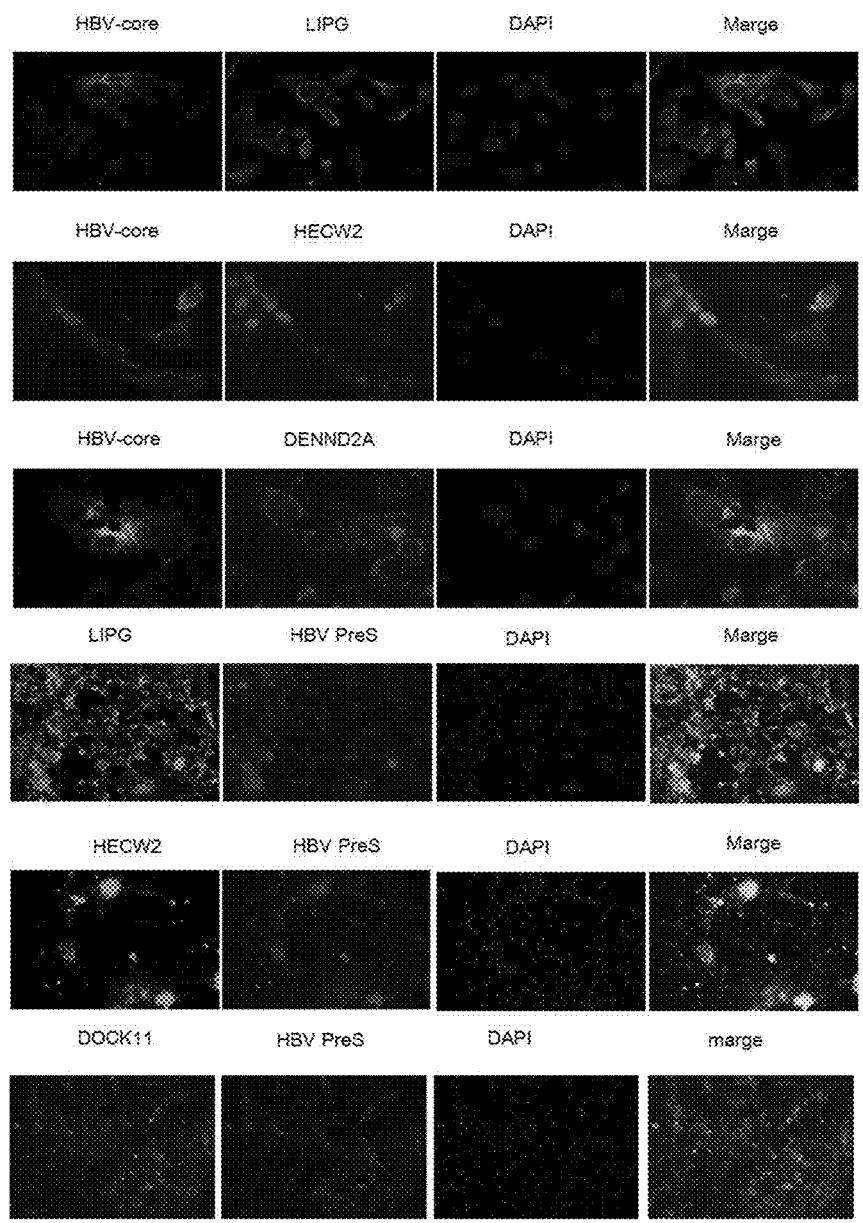
FIG. 16 depicts images showing the localization of individual proteins investigated by indirect immunostaining in a human hepatocellular carcinoma cell line established from a hepatitis B-positive patient with hepatocellular carcinoma. (Example 7)

The results are shown in FIG. 16. DOCK11 was found to localize at the same position as the HBV proteins.

(Example 8) Confirmation of shRNA Function Against HCV

The antiviral activity of the shRNA against Dock11 gene was evaluated using a replicon system for JFH1 strain. HCV replication analysis was performed by transfecting Huh 7.5 cells with synthetic JFH1-RNA. Cells in which DOCK11 was constitutively knocked down were prepared by introducing DOCK11 shRNA #2 into Huh 7.5 cells. Cells into which cont shRNA was introduced were used as a control. Huh 7.5 cells into which each shRNA had been introduced were transfected with 1 µg synthetic RNA (JFH1-RNA) using TransIT®-mRNA Transfection Kit (Mirus). Total RNAs were isolated 24, 48 and 72 hours after the transfection using High Pure RNA Isolation Kit (Roche), and cDNAs were synthesized using high-capacity cDNA reverse transcription kit (Applied Biosystems, Carlsbad, Calif.). HCV RNA was detected in the same manner as described in Shirasaki, T. et al. J Infect Dis 202, 75-85, doi: 10.1086/653081 (2010). The expression of DOCK11 gene was evaluated by determining the level of mRNA in the same manner as in Example 2.

Figure 17:
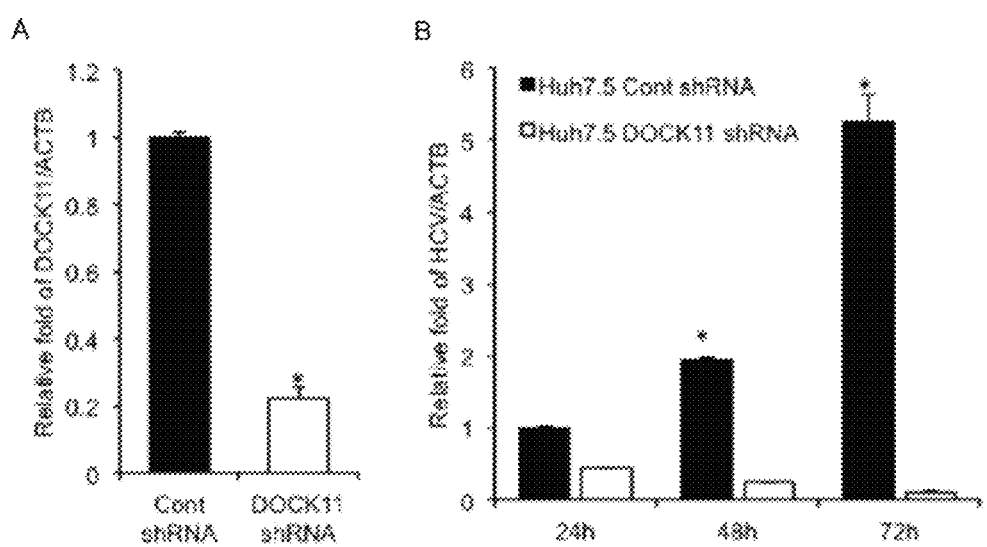
FIG. 17 shows the effects of introduction of shRNAs against DOCK11 gene and subsequent culturing on: the expression level of DOCK11 gene (A); and the relative amount of HCV (B), which were investigated using a hepatitis C virus (HCV) infection system in human hepatocytes. The expression levels are expressed as relative values by taking the control level (Cont shRNA) as 1. (Example 8)

The results are shown in FIG. 17. The expression level of DOCK11 gene in Huh7.5 cells was decreased by the shRNA against DOCK11 gene. It was also found that HCV replication in Huh7.5 cells was suppressed by the shRNA against DOCK11 gene. It was found that HCV RNA replication was effectively suppressed at 1 to 3 days (24, 48 and 72 hours) after the introduction of HCV RNA.

(Example 9) Inhibition of Expression of Target Gene by Pyrrole-Imidazole Polyamide To HepG2.2.15 cells, which were established by transfecting HepG2 human hepatoma cells with HBV, pyrrole-imidazole polyamide capable of specifically binding to the target gene is added at 5 µM from the start of culturing, and time-dependent changes are observed. After a certain period of time, the cells are collected and the mRNA expression level of DOCK11 gene, and the amounts of HBV DNA, HBV cccDNA and pg RNA are measured in the same manner as in Examples 1 and 2.

(Example 10) Determination of Effect of LIPG Inhibitor on HBV

An HBV expression construct (HBV-C: provided by Dr. Yasuhito Tanaka at Nagoya City University) was introduced into Huh7 cell line. Five days after the introduction, an LIPG inhibitor (GSK264220A) was added at 1 µM to 100 µM and the cells were cultured. One week after the addition of the LIPG inhibitor, the amounts of HBV DNA and HBV cccDNA were determined in the same manner as in Examples 1 and 2.

The results are shown in FIG. 20. It was confirmed that, depending on the concentration of the LIPG inhibitor, the amounts of HBV DNA and HBV cccDNA were decreased and HBV infection was inhibited.

(Example 11) Determination of shRNA Function Against Cdc42 Gene

Five shRNAs were prepared against Cdc42 gene, which is a gene encoding Cdc42 known to interact with DOCK11 although no difference was observed in its expression level for HBV gene retention, and investigated for their antiviral actions against hepatitis B virus in the same manner as in Example 2.

HepG2.2.15 cells were infected with lentiviruses expressing individual shRNAs against the Cdc42 gene (Sigma-Aldrich Japan K.K., Tokyo, Japan, TRCN0000047631, TRCN0000047629, TRCN0000047628, 1RCN0000047632, TRCN0000310772; sequences #1 to #5 of five shRNAs are shown below) according to a conventional method, and 1 week later, the amounts of HBV DNA and HBV cccDNA were determined. The amounts of HBV DNA and HBV cccDNA were measured in the same manner as in Example 1.

```
CDC42 shRNA #1:
                                    (SEQ ID NO: 55)
CCGGCCAAGAACAAACAGAAGCCTACTCGAGT
AGGCTTCTGTTTGTTCTTGGTTTTTG

CDC42 shRNA #2:
                                    (SEQ ID NO: 56)
CCGGCGGAATATGTACCGACTGTTTCTCGAGA
AACAGTCGGTACATATTCCGTTTTTG

CDC42 shRNA #3:
                                    (SEQ ID NO: 57)
CCGGCCCTCTACTATTGAGAAACTTCTCGAGAA
GTTTCTCAATAGTAGAGGGTTTTG

CDC42 shRNA #4:
                                    (SEQ ID NO: 58)
CCGGCAGATGTATTTCTAGTCTGTTCTCGAGAA
CAGACTAGAAATACATCTGTTTTTG

CDC42 shRNA #5:
                                    (SEQ ID NO: 59)
CCGGGACTCTGTAACAGACTAATTGCTCGAGC
AATTAGTCTGTTACAGAGTCTTTTTG
```

Figure 21:
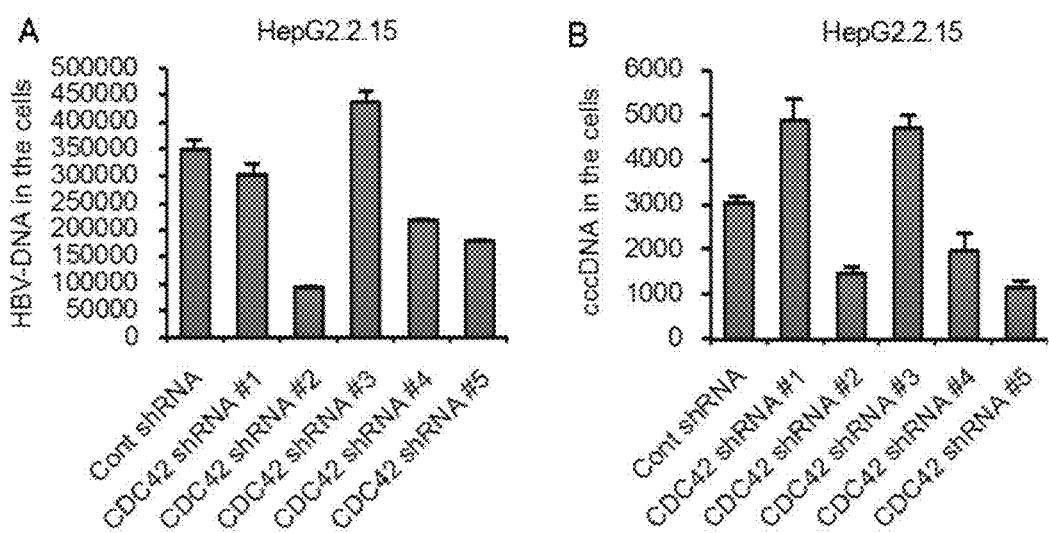
FIG. 21 shows the effects of introduction of an shRNA against Cdc42 gene on: the amount of HBV DNA (A); and the amount of HBV cccDNA (B), which were investigated using an HBV infection system in human hepatocytes. (Example 11)

The results are shown in FIG. 21. It was found that the amounts of HBV DNA and cccDNA could be decreased by using the shRNAs against Cdc42 gene.

(Example 12) Determination of shRNA Function Against Influenza Viral Infection

The behavior of nucleoprotein of influenza virus in A549 cells, a lung adenocarcinoma cell line, was investigated when the cells were infected with influenza virus and then shRNA against DOCK11 or Cdc42 gene was introduced to the cells.

First, A549 cells were seeded on a 10 cm dish. After seeding, A549 cells were infected with lentivirus comprising any one of cont shRNA, DOCK11 shRNA #2, and CDC42 shRNAs #1 to #5 in the same manner as in Examples 2 and 11. Forty eight hours after the infection, 5 μg/ml of puromycin was added. Thereafter, the cells were cultured for 1 week, and then cells into which shRNA was introduced were selected. The selected cells were seeded on a chamber slide. The cells were infected with influenza virus (WSN strain) (obtained from Dr. Masayoshi Enami at Kanazawa University) isolated from MDCK cells. Twenty four hours after the infection with influenza virus, the cells were fixed with acetone and methanol, and then influenza nucleoproteins (NPs) were immunostained using Influenza A H1N1 HA Antibody (Thermo Fisher PAS-34929) and observed.

Figure 22:
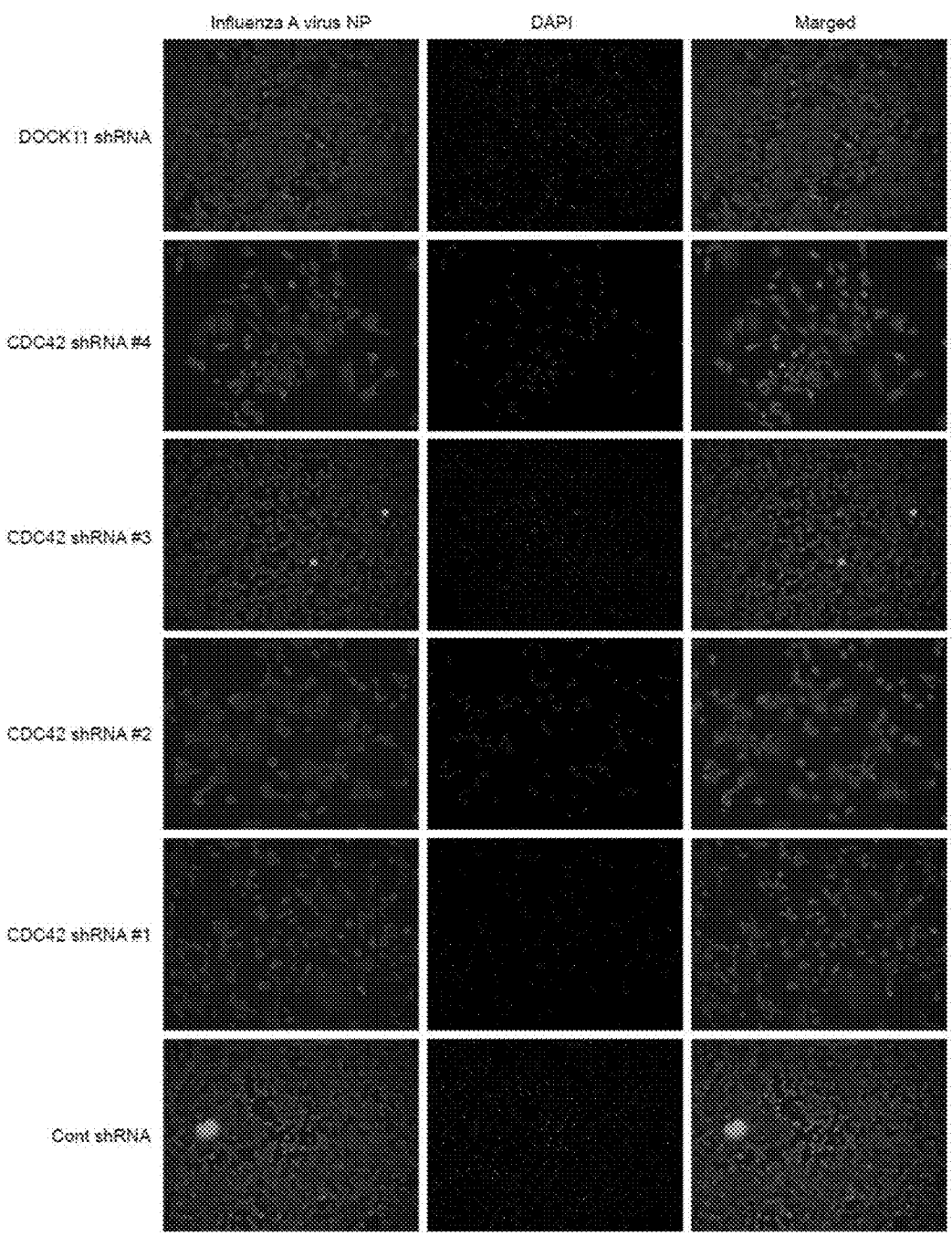
FIG. 22 shows the behavior of nucleoprotein of influenza virus in cells into which shRNA against DOCK11 or Cdc42 gene was introduced, which was investigated using an infection system of a lung adenocarcinoma cell line A549 infected with influenza virus. (Example 12)

The results are shown in FIG. 22. It was confirmed that localization of nucleoproteins of influenza virus in the nucleus of the host cell was suppressed when shRNA for DOCK11 gene or Cdc42 gene was introduced. This suggested that DOCK11 is involved in replication of influenza virus.

INDUSTRIAL APPLICABILITY

The antiviral drug of the present invention can greatly reduce the amount of HBV cccDNA compared to conventional growth inhibitors for hepatitis B virus, and has a potential to completely remove it. The antiviral drug of the present invention is thought to have a different mechanism of action from conventional antiviral drugs and act on the transport pathway to the nuclei after virus enters across the membrane on the surface of host cells. Therefore, it is contemplated that the antiviral drug of the present invention exhibits an antiviral effect not only on HBV but on various viruses. Further, it is contemplated that the antiviral drug of the present invention exerts an antiviral effect synergistically in combination with a conventional antiviral drug. The antiviral drug of the present invention is expected to enable prevention of viral infection, and remission or radical cure of viral infection, and to contribute greatly to treatment of diseases due to viral infection. Furthermore, by using the target gene of the present invention as an indicator, screening for an antiviral drug based on a novel mechanism can be achieved.

---

The invention claimed is:

1. A method for treatment and/or prevention of a disease associated with viral infection in a mammal, comprising administering to the mammal a substance capable of suppressing an expression of a target gene or an activity of a protein encoded by said target gene, wherein said target gene is one or more genes having an action of retaining virus-derived nucleic acid in a host cell and selected from the group consisting of DOCK11 gene, LIPG gene, DENND2A gene, and HECW2 gene.

2. The method according to claim 1, wherein the target gene is DOCK11 gene.

3. The method according to claim 1, wherein the substance capable of suppressing the expression of the target gene or the activity of the protein encoded by the target gene is one or more compounds selected from the group consisting of shRNA, siRNA, miRNA, antisense oligonucleotide, and pyrrole-imidazole polyamide for the target gene or transcription product thereof.

4. The method according to claim 1, wherein the substance capable of suppressing the expression of the target gene or the activity of the protein encoded by the target gene recognizes a base sequence selected from any of the followings:

(SEQ ID NO: 36) CCAACAGGGTGCTTACATATT (SEQ ID NO: 37) GTACTAGACACCATATCATTT (SEQ ID NO: 38) ACTAAATGAGCGGCTAATTAA (SEQ ID NO: 39) TGATGGCCATAACCCATTAAT (SEQ ID NO: 40) CCAGGCTACTTGAATCTGAAT (SEQ ID NO: 41) CTGAAGGGACTAGGCAATAAA (SEQ ID NO: 42) CCAATGAAGGAGAACCCTTAT (SEQ ID NO: 43) CCTAGTGCAGCCCTATTCTTT (SEQ ID NO: 44) CTAGTGCAGCCCTATTCTTTA

-continued (SEQ ID NO: 45) ACGATGTCTTGGGATCAATTG (SEQ ID NO: 46) ATGCAGGCAACTTCGTGAAAG (SEQ ID NO: 47) CCGTTGTAATAGCATTGGCTA (SEQ ID NO: 48) CGTCACCCTTTATGGCACTAA (SEQ ID NO: 49) TTACACGGATGCGGTCAATAA (SEQ ID NO: 50) GCCCAAACATTTCTTTGAGAT (SEQ ID NO: 51) CCAGGGAAGTTAAAGTTAATT (SEQ ID NO: 52) GCACAATACTTGGAGTCAATT (SEQ ID NO: 53) GCTTACAATGACAAGATTGTT (SEQ ID NO: 54) CCCTTATCTTAAGATGTCAAT a base sequence obtained by substituting, deleting, adding and/or inserting one to several bases in any one of the base sequences of the above-described SEQ ID NOs: 36 to 54.

5. The method according to claim 1, wherein the substance capable of suppressing the expression of the target gene or the activity of the protein encoded by the target gene is an shRNA comprising a base sequence selected from any of the followings:

(SEQ ID NO: 1) CCGGCCAACAGGGTGCTTACATATTCTCGAGAATATGTAAGCACCCTGTTGGTTTTTG (SEQ ID NO: 2) CCGGGTACTAGACACCATATCATTTCTCGAGAAATGATATGGTGTCTAGTACTTTTTG (SEQ ID NO: 3) CCGGACTAAATGAGCGGCTAATTAACTCGAGTTAATTAGCCGCTCATTTAGTTTTTG

-continued

```
                                                      (SEQ ID NO: 4)
CCGGTGATGGCCATAACCCATTAATCTCGAGATTAATGGGTTATGGCCA
TCATTTTTG (SEQ ID NO: 5)
CCGGCCAGGCTACTTGAATCTGAATCTCGAGATTCAGATTCAAGTAGCC
TGGTTTTTG (SEQ ID NO: 6)
CCGGCTGAAGGGACTAGGCAATAAACTCGAGTTTATTGCCTAGTCCCTT
CAGTTTTTG (SEQ ID NO: 7)
CCGGCCAATGAAGGAGAACCCTTATCTCGAGATAAGGGTTCTCCTTCAT
TGGTTTTTTG (SEQ ID NO: 8)
CCGGCCTAGTGCAGCCCTATTCTTTCTCGAGAAAGAATAGGGCTGCACT
AGGTTTTTG (SEQ ID NO: 9)
CCGGCTAGTGCAGCCCTATTCTTTACTCGAGTAAAGAATAGGGCTGCAC
TAGTTTTTG (SEQ ID NO: 10)
CCGGACGATGTCTTGGGATCAATTGCTCGAGCAATTGATCCCAAGACAT
CGTTTTTG (SEQ ID NO: 11)
CCGGATGCAGGCAACTTCGTGAAAGCTCGAGCTTTCACGAAGTTGCCT
GCATTTTTG (SEQ ID NO: 12)
CCGGCCGTTGTAATAGCATTGGCTACTCGAGTAGCCAATGCTATTACAA
CGGTTTTTG (SEQ ID NO: 13)
CCGGCGTCACCCTTTATGGCACTAACTCGAGTTAGTGCCATAAAGGGTG
ACGTTTTTG (SEQ ID NO: 14)
CCGGTTACACGGATGCGGTCAATAACTCGAGTTATTGACCGCATCCGTG
TAATTTTTG (SEQ ID NO: 15)
CCGGGCCCAAACATTTCTTTGAGATCTCGAGATCTCAAAGAAATGTTTG
GGCTTTTT (SEQ ID NO: 16)
CCGGCCAGGGAAGTTAAAGTTAATTCTCGAGAATTAACTTTAACTTCCC
TGGTTTTT (SEQ ID NO: 17)
CCGGGCACAATACTTGGAGTCAATTCTCGAGAATTGACTCCAAGTATTG
TGCTTTTT (SEQ ID NO: 18)
CCGGGCTTACAATGACAAGATTGTTCTCGAGAACAATCTTGTCATTGTA
AGCTTTTT (SEQ ID NO: 19)
CCGGCCCTTATCTTAAGATGTCAATCTCGAGATTGACATCTTAAGATAA
GGGTTTTT
``` a base sequence obtained by substituting, deleting, adding and/or inserting one to several bases in any one of the base sequences of the above-described SEQ ID NOs: 1 to 19.

6. The method according to claim 1, wherein the viral infection is infection with a virus(es) selected from hepatitis B virus, hepatitis C virus, hepatitis A virus, hepatitis E virus, influenza virus, human immunodeficiency virus, RS virus, papillomavirus, adenovirus, poliovirus, echovirus, coxsackievirus, enterovirus, rhinovirus, rotavirus, norovirus, Newcastle disease virus, mumps virus, vesicular stomatitis virus, rabies virus, Lassa virus, measles virus, rubella virus, filovirus, Ebola virus, Japanese encephalitis virus, yellow fever virus, dengue virus, West Nile virus, and Zika virus.

7. The method according to claim 1, wherein the viral infection is infection with a hepatitis virus.

8. The method according to claim 1, wherein the viral infection is infection with a hepatitis B virus.

9. The method according to claim 1, which is used in combination with a viral growth inhibitor.

10. A screening method for an antiviral drug, comprising selecting, as an antiviral drug, a substance capable of suppressing an expression of a target gene or an activity of a protein encoded by said target gene from test substances, wherein said target gene is one or more genes having an action of retaining virus-derived nucleic acid in a host cell and selected from the group consisting of DOCK11 gene, LIPG gene, DENND2A gene, and HECW2 gene.

11. The screening method for an antiviral drug according to claim 10, the method comprising the following steps (A) to (C) of:
  (A) bringing a cell into contact with a test substance in a system in which the cell expresses the target gene;
  (B) measuring the expression level of the target gene in the cell and comparing the expression level of the target gene in the cell contacted with the test substance to the expression level of the target gene in the cell not contacted with the test substance;
  (C) selecting a test substance that causes a decrease in the expression level of the target gene in the cell as an antiviral drug through screening based on the comparison result in step (B) above.

12. The screening method for an antiviral drug according to claim 10, the method comprising the following steps (a) to (c) of:
  (a) bringing a protein encoded by the target gene into contact with a protein that interacts with the protein encoded by the target gene in the presence of a test substance;
  (b) measuring the binding ability between the protein encoded by the target gene and the protein that interacts with the protein encoded by the target gene, and comparing the binding ability in the presence of the test substance to the binding ability in the absence of the test substance;
  (c) selecting a test substance that causes a decrease in the binding ability between the protein encoded by the target gene and the protein that interacts with the protein encoded by the target gene as an antiviral drug based on the comparison result in step (b) above.

13. The screening method for an antiviral drug according to claim 10, the method comprising the following steps (a) to (c) of:
  (a) bringing a protein encoded by the target gene into contact with a substrate for the protein encoded by the target gene in the presence of a test substance;
  (b) measuring the enzymatic activity of the protein encoded by the target gene, and comparing the enzymatic activity in the presence of the test substance to the enzymatic activity in the absence of the test substance;
  (c) selecting a test substance that causes a decrease in the enzymatic activity of the protein encoded by the target gene as an antiviral drug based on the comparison result in step (b) above.

14. A method for treatment and/or prevention of a disease associated with viral infection in a mammal, comprising administering to the mammal an antiviral drug selected through screening by the screening method for an antiviral drug according to claim 10.

15. A screening method for an antiviral drug, comprising selecting, as an antiviral drug, a substance capable of suppressing an expression of a target gene or an activity of a protein encoded by said target gene from test substances, wherein said target gene is a gene having an action of retaining virus-derived nucleic acid in a host cell, wherein the gene is selected by analyzing a host cell after viral infection for the expression patterns of two or more finite numbers of genes, and detecting the gene having an action of retaining virus-derived nucleic acid in the host cell from host cell-derived genes.

16. A method for producing an antiviral drug, comprising obtaining an antiviral drug through screening by the screening method according to claim 10, and formulating the antiviral drug into a solid formulation or a liquid formulation.

17. The method of claim 1, wherein the mammal is an animal.

* * * * *